(12) United States Patent
Gendelman et al.

(10) Patent No.: US 12,257,306 B2
(45) Date of Patent: Mar. 25, 2025

(54) ANTIVIRAL PRODRUGS AND NANOFORMULATIONS THEREOF

(71) Applicant: Board of Regents of the University of Nebraska, Lincoln, NE (US)

(72) Inventors: Howard E. Gendelman, Omaha, NE (US); Benson Edagwa, Omaha, NE (US)

(73) Assignee: Board of Regents of the University of Nebraska, Lincoln, NE (US)

(*) Notice: Subject to any disclaimer, the term of this patent is extended or adjusted under 35 U.S.C. 154(b) by 0 days.

(21) Appl. No.: 18/050,351

(22) Filed: Oct. 27, 2022

(65) Prior Publication Data

US 2024/0100171 A1 Mar. 28, 2024

Related U.S. Application Data

(63) Continuation of application No. 17/309,435, filed as application No. PCT/US2019/063498 on Nov. 27, 2019.

(60) Provisional application No. 62/772,852, filed on Nov. 29, 2018.

(51) Int. Cl.
A61K 47/55 (2017.01)
A61K 9/14 (2006.01)
A61P 31/18 (2006.01)

(52) U.S. Cl.
CPC .............. *A61K 47/55* (2017.08); *A61K 9/146* (2013.01); *A61P 31/18* (2018.01)

(58) Field of Classification Search
CPC ........ A61K 47/55; A61K 9/146; A61K 9/145; A61P 31/18; C07D 215/56; C07D 498/14; C07D 498/18; C07D 519/00; C07D 413/14
See application file for complete search history.

(56) References Cited

U.S. PATENT DOCUMENTS

| | | | |
|---|---|---|---|
| 9,216,996 B2 | 12/2015 | Jin et al. | |
| 9,758,515 B2 | 9/2017 | Takahashi et al. | |
| 11,117,904 B2 | 9/2021 | Edagwa et al. | |
| 11,154,557 B2 | 10/2021 | Gendelman et al. | |
| 11,166,957 B2 | 11/2021 | Gendelman et al. | |
| 11,311,547 B2 | 4/2022 | Gendelman et al. | |
| 2011/0183940 A1 | 7/2011 | Johns et al. | |
| 2013/0171214 A1 | 7/2013 | Mundhra et al. | |
| 2014/0011995 A1 | 1/2014 | Sumino et al. | |
| 2014/0221378 A1 | 8/2014 | Miyazaki et al. | |
| 2015/0050241 A1 | 2/2015 | Volinsky et al. | |
| 2015/0232479 A1 | 8/2015 | Johns et al. | |
| 2015/0297587 A1 | 10/2015 | Gelbard et al. | |
| 2016/0184332 A1 | 6/2016 | Renner | |
| 2017/0326103 A1 | 11/2017 | Porter et al. | |
| 2018/0051043 A1 | 2/2018 | Yu et al. | |

(Continued)

FOREIGN PATENT DOCUMENTS

| | | |
|---|---|---|
| WO | WO-2010011814 A1 | 1/2010 |
| WO | WO-2012061480 A2 | 5/2012 |

(Continued)

OTHER PUBLICATIONS

Co-Pending U.S. Appl. No. 17/301,030, filed Mar. 22, 2021.

(Continued)

*Primary Examiner* — Rayna Rodriguez

(74) *Attorney, Agent, or Firm* — COOLEY LLP

(57) ABSTRACT

The present invention provides prodrugs and methods of use thereof.

8 Claims, 6 Drawing Sheets

(56) References Cited

U.S. PATENT DOCUMENTS

Figure 1:
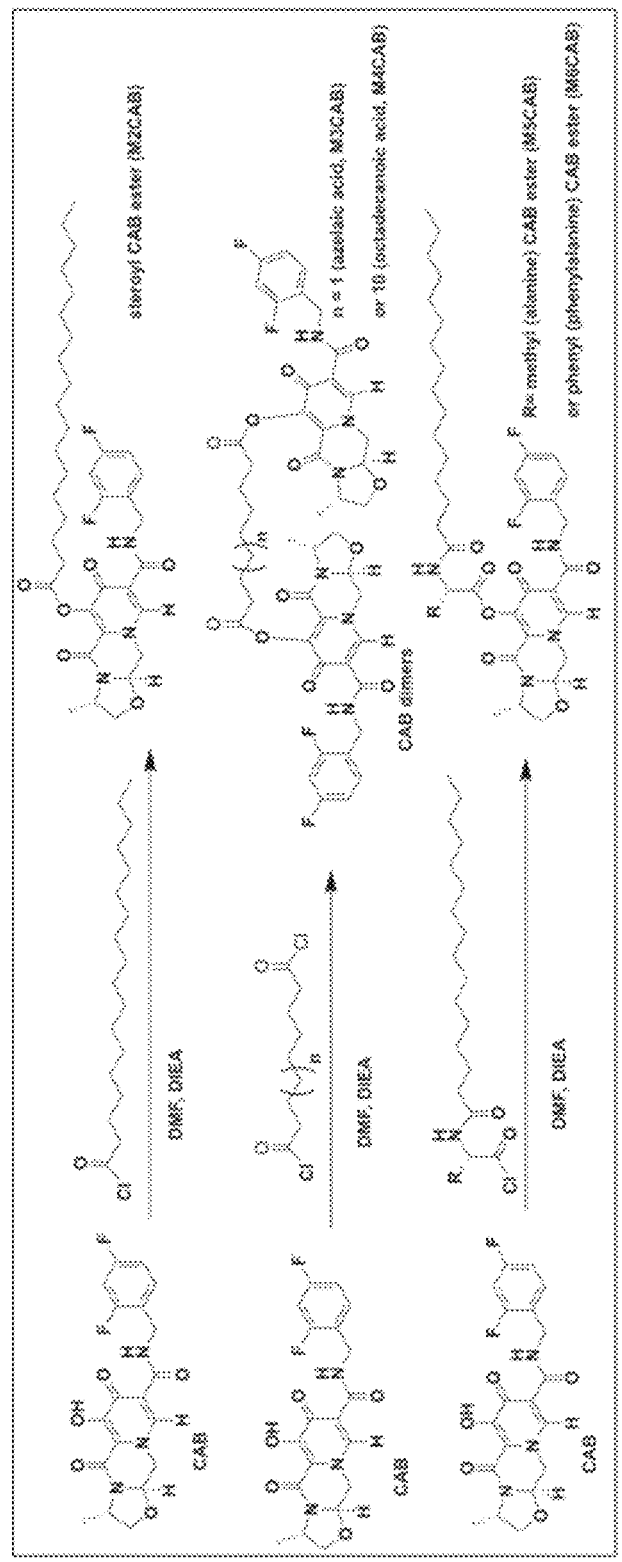

| | | |
|---|---|---|
| 2021/0275535 A1 | 9/2021 | Gendelman et al. |
| 2021/0322425 A1 | 10/2021 | Gendelman et al. |
| 2022/0175936 A1 | 6/2022 | Gendelman et al. |
| 2022/0211716 A1 | 7/2022 | Gendelman et al. |

FOREIGN PATENT DOCUMENTS

| | | |
|---|---|---|
| WO | WO-2014200880 A1 | 12/2014 |
| WO | WO-20170223280 A2 | 12/2017 |
| WO | WO-2020086555 A1 | 4/2020 |
| WO | WO-2020112931 A1 | 6/2020 |
| WO | WO-2022/099431 A1 | 5/2022 |

OTHER PUBLICATIONS

Co-Pending U.S. Appl. No. 17/303,228, filed May 24, 2021.
Co-Pending U.S. Appl. No. 17/303,229, filed May 24, 2021.
Dolutegravir, Wikipedia (5 pages) (2023).
EP Search Report EP 23 16 0610, dated Aug. 8, 2023 (3 pages).
EP Search Report EP 23 16 0303, dated Aug. 9, 2023 (3 pages).
Goldstein et al., "Incidence of class 1 and class 2 integrases in clinical and commensal bacteria from liverstock, Companion animals and exotics," Antimicrobial Agents and Chemotherapy, vol. 45(3): 723-726 (2001).
Integrase, Wikipedia (5 pages) (2023).
Retrovirus, Wikipedia (7 pages) (2023).
Andrews, C.D., et al., A long-acting integrase inhibitor protects female macaques from repeated high-dose intravaginal SHIV challenge, Sci Transl Med, 7(270): 270ra4 (2015).
Andrews, C.D., et al., Long-Acting Integrase Inhibitor Protects Macaques from Intrarectal Simian/Human Immunodeficiency Virus, Science, 343(6175): 1151-1154 (2014).
Application of Harold G. Petering and Harry H. Fall, Patent Appeal No. 6750, United States Court of Customs and Patent Appeals, Apr. 13, 1962.
Edgawa, B., et al., Long acting slow effective release antiretroviral therapy, Expert Opin Drug Deliv, 14(11): 1281-1291 (2017).
Gautam, N., et al., Lipophilic nanocrystal prodrug-release defines the extended pharmacokinetic profiles of a year-long cabotegravir, Nat Commun, 12(1): 3453 (2021).
Gendelman, H.E., et al., The promise of long acting antiretroviral therapies: From need to manufacture, Trends Microbiol, 27(7): 593-606 (2019).
Ikuta, Y., et al., The effect of molecular structure on the anticancer drug release rate from prodrug nanoparticles, Chem Commun (Camb), 51(64): 12835-12838 (2015).
Kulkarni, T.A., et al., A year-long extended release nanoformulated cabotegravir prodrug, Nat Mater, 19(8): 910-920 (2020).
Landovitz, R.J., et al., Safety, tolerability, and pharmacokinetics of long-acting injectable cabotegravir in low-risk HIV-uninfected individuals: HPTN 077, a phase 2a randomized controlled trial, PLoS Med, 15(11):e1002690 (2018).
Long, Y., et al., Rational design and synthesis of novel dimeric diketoacid-containing inhibitors of HIV-1 integrase: implication for binding to two metal ions on the active site of integrase, J Med Chem, 47(10): 2561-2573 (2004).
Margolis, D.A., et al., Long-acting intramuscular cabotegravir and rilpivirine in adults with HIV-1 infection (LATTE-2): 96-week results of a randomised, open-label, phase 2b, non-inferiority trial, Lancet, 390(10101): 1499-1510 (2017).
Markowitz, M., et al., Safety and tolerability of long-acting cabotegravir injections in HIV-uninfected men (ECLAIR): a multicentre, double-blind, randomised, placebo-controlled, phase 2a trial, Lancet HIV, 4(8): e331-e340 (2017).
McMillan, J., et al., Pharmacokinetic testing of a first-generation cabotegravir prodrug in rhesus macaques, AIDS, 33(3): 585-588 (2019).
McMillan, J., et al., Pharmacokinetics of a long-acting nanoformulated dolutegravir prodrug in rhesus macaques, Antimicrob Agents Chemother, 62(1): e01316-e01317 (2018).
Namanja, H.A., et al., Toward eradicating HIV reservoirs in the brain: inhibiting P-glycoprotein at the blood-brain barrier with prodrug abacavir dimers, J Am Chem Soc, 134(6): 2976-2980 (2012).
PCT/US2017/038693 International Search Report and Written Opinion dated Nov. 27, 2017.
PCT/US2019/057406 International Search Report and Written Opinion dated Jan. 16, 2020.
PCT/US2019/063498 International Search Report and Written Opinion dated Apr. 8, 2020.
Radzio, J., et al., The long-acting integrase inhibitor GSK744 protects macaques from repeated intravaginal SHIV challenge, Sci Transl Med, 7(270): 270ra5 (2015).
Sillman, B., et al., Creation of a long-acting nanoformulated dolutegravir, Nat Commun, 9(1): 443 (2018).
Spreen, W., et al., GSK1265744 pharmacokinetics in plasma and tissue after single-dose long-acting injectable administration in healthy subjects, J Acquir Immune Defic Syndr, 67(5): 481-486 (2014).
Spreen, W.R., et al., Long-acting injectable antiretrovirals for HIV treatment and prevention, Curr Opin Hiv Aids, 8(6): 565-571 (2013).
Stellbrink, H-J, et al., Cabotegravir: its potential for antiretroviral therapy and preexposure prophylaxis, Curr Opin Hiv Aids, 13(4): 334-340 (2018).
Trezza. C.,et al., Formulation and pharmacology of long-acting cabotegravir, Curr Opin Hiv Aids, 10(4): 239-245 (2015).
U.S. Appl. No. 17/301,030 Office Action dated May 27, 2021.
U.S. Appl. No. 17/303,228 Office Action dated Aug. 11, 2021.
U.S. Appl. No. 17/303,229 Office Action dated Aug. 25, 2021.
Zaro, J.L., et al., Lipid-based drug carriers for prodrugs to enhance drug delivery, Aaps J, 17(1): 83-92 (2015).
Zhou, T., et al., A long-acting nanoformulated cabotegravir prodrug for improved antiretroviral therapy, Topics in Antiviral Medicine, 25(Supplement 1): 180s-181s, Abstract Number: 439. EMBASE Document No. 616686282 (2017).
Zhou, T., et al., Creation of a nanoformulated cabotegravir prodrug with improved antiretroviral profiles, Biomaterials, 151: 53-65 (2018).
Zhou, T., Next generation of trasnslational long-acting cabotegravir, Electronic Theses and Dissertations University of Nebraska Medical Center, 139 pages (2018).
Soriano et al., Long-acting antiretroviral therapy, Nature Materials, vol. 19:826-827 (2020).

ANTIVIRAL PRODRUGS AND NANOFORMULATIONS THEREOF

CROSS REFERENCE

This application is a continuation of U.S. application Ser. No. 17/309,435 filed May 27, 2021, which is a national entry under 35 U.S.C. § 371 of International Application No. PCT/US2019/063498, filed Nov. 27, 2019 (now published), which claims priority under 35 U.S.C. § 119(e) to U.S. Provisional Application No. 62/772,852, filed Nov. 29, 2018. The forgoing applications are incorporated by reference herein.

STATEMENT AS TO FEDERALLY SPONSORED RESEARCH

This invention was made with government support under Grants Nos. R01 MH104147, P01 DA028555, R01 NS036126, P01 NS031492, R01 NS034239, P01 MH064570, P30 MH062261, P30 AI078498, R01 AG043540, R56 AI138613, and R01 AI158160 awarded by the National Institutes of Health. The government has certain rights in the invention.

FIELD OF THE INVENTION

The present invention relates generally to the delivery of therapeutics. More specifically, the present invention relates to compositions and methods for the delivery of therapeutic agents to a patient for the treatment of a disease or disorder.

BACKGROUND OF THE INVENTION

Remarkable progress has been made in the development of effective diagnostics and treatments against human immunodeficiency virus type one (HIV-1). Antiretroviral therapy (ART) has markedly reduced disease-associated morbidities and mortality, enabling a nearly normal quality of life for infected people (Vittinghoff, et al. (1999) J. Infect Dis., 179(3):717-720; Lewden, et al. (2007) J. Acquir. Immune Defic. Syndr., 46(1):72-77). However, ART requires lifelong treatment in order to suppress viral replication and prevent AIDS onset. Moreover, the effectiveness of ART can be hampered by HIV-1 resistance, drug toxicities, and poor patient adherence (Wensing, et al. (2014) Top. Antivir. Med., 22(3):642-650; Siliciano, et al. (2013) Curr. Opin. Virol., 3(5):487-494; Prosperi, et al. (2012) BMC Infect. Dis., 12:296-296; Van den Berk, et al. (2016) Abstract number: 948, In Conference on Retroviruses and Opportunistic Infections, 22-25; Siefried, et al. (2017) PLoS One 12(4): e0174613). Treatment fatigue, lack of financial and social support, co-existing mental symptoms, and/or substance abuse can result in the failure to adhere to critical ART regimens (Tucker, et al. (2017) EBioMedicine, 17:163-171).

It is now well accepted that long-acting antiretroviral drugs (ARVs) can reduce viral transmission, prevent new infection, affect regimen adherence and limit the emergence of viral drug resistance and systemic toxicities (Spreen, et al. (2013) Curr. Opin. HIV AIDS 8:565-71; Williams, et al. (2013) Nanomedicine (Lond) 8:1807-13). Poloxamer-coated nanocrystals were made from insoluble compounds as long acting parenterals (LAP) (Rabinow, B. E. (2004) Nat. Rev. Drug Discov., 3:785-96). Long-acting parenteral (LAP) antiretroviral drugs have improved regimen adherence (Spreen, et al. (2013) Curr. Opin. HIV AIDS, 8(6):565-571). Reducing the treatment schedule from daily to monthly or even less-frequent administration provides greater patient privacy and satisfaction and improves regimen adherence (Sangaramoorthy, et al. (2017) J. Assoc. Nurses AIDS Care, 28(4):518-531; Carrasco, et al. (2017) Afr. J. AIDS Res. 16(1):11-18; Williams, et al. (2013) Nanomed. Lond. 8(11):1807-1813). However, only a few antiretroviral drugs have been successfully reformulated into LAPs.

The most notable ARV LAPs are cabotegravir (CAB) and rilpivirine (RPV), which when administered once/month can elicit comparable antiretroviral activity to daily oral three-drug combinations for maintenance therapy (Margolis, et al. (2017) Lancet 390:1499-510). However, there are limitations to any widespread use of CAB RPV LAP combinations as they require large injection volumes, show injection site reactions with limited drug access to infectious reservoirs (Zhou, et al. (2018) Biomaterials 151:53-65; Margolis, et al. (2017) Lancet 390:1499-510; Markowitz, et al. (2017) Lancet HIV 4:e331-e40).

CAB is an integrase inhibitor or integrase strand transfer inhibitor (INSTI) with low aqueous solubility, high melting point, high potency, long half-life, and slow metabolic clearance (Karmon, et al. (2015) J. Acquir. Immune Defic. Syndr., 68(3):39-41; Trezza, et al. (2015) Curr. Opin. HIV AIDS 10(4):239-245). These properties enable CAB to be formulated in a 200-mg/mL suspension (CAB LAP) and administered intramuscularly monthly or even less frequently (Margolis, et al. (2017) Lancet 390(10101):1499-1510; Spreen, W. W. (2014) J. Acquir. Immune Defic. Syndr., 67(5):481-486). Notably, CAB plus rilpivirine (RPV) is the first long-acting combination ART regimen where monthly or every other month CAB and RPV LAP formulations have demonstrated comparable antiretroviral activity to daily oral three-drug combinations for maintenance therapy (Margolis, et al. (2017) Lancet 390(10101): 1499-1510).

However, the dosing pattern of CAB LAP has limitations. Specifically, split injections given in 2 mL volumes are required which leads to treatment cessations because of intolerable injection site reactions (Margolis, et al. (2017) Lancet 390(10101):1499-510; Markowitz, et al. (2017) Lancet HIV 4(8):331-340). Moreover, the maximal dosing interval is only 8 weeks. Recently, the administration of CAB LAP every 12 weeks has been tested with the aim of maintaining plasma CAB concentrations above 4 times protein-binding-adjusted 90% inhibitory concentration ($4 \times PA\text{-}IC_{90}$, 660 ng/mL), a concentration demonstrated to be protective against new infections in macaques (Spreen, W. W. (2014) J. Acquir. Immune Defic. Syndr., 67(5):481-486; Andrews, et al. (2014) Science 343(6175):1151-1154; Andrews, et al. (2015) Sci. Transl. Med., 7(270) 270ra4; Radzio, et al. (2015) Sci. Transl. Med., 7(270) 270ra5-270ra5; Andrews, et al. (2016) AIDS 2016:461-467; Markowitz, et al. (2017) Lancet HIV 4(8):331-340; Spreen, et al. (2014) J. Acquir. Immune Defic. Syndr., 67(5):487-492). However, two-thirds of participants had faster than anticipated drug absorption leading to plasma drug concentrations below the targeted effective concentration of $4 \times PA\text{-}IC_{90}$ at 12 weeks. Thus, ways to extend the dose interval beyond 8 weeks and reduce injection volumes to improve regimen adherence are greatly needed (Boyd, et al. (2017) Lancet 390(10101):1468-1470).

Complementary to LAP ARVs are preclinical implantable devices for longer sustained release. Each can facilitate the other with a noted exception. Indeed, the implantable devices require professional insertion and monitoring. Further, limitations exist in scale up and processing including a potential for "drug dumping" from biodegradable polymers. In addition, toxicity from organic solvents and high gel viscosity can provide local irritation (Kranz, et al. (2001) Int. J. Pharm., 212:11-8). While biodegradable implants provide some additional benefits, removals for adverse events or local trauma remains challenging.

In view of the foregoing, it is clear that improved long term delivery of ART is needed.

SUMMARY OF THE INVENTION

In accordance with the instant invention, prodrugs of integrase inhibitors are provided. In some embodiments, the prodrug is a dimer of integrase inhibitors connected by a linker (e.g., an optionally substituted aliphatic or alkyl group). In some embodiments, the prodrug comprises an integrase inhibitor modified with an amino acid fatty ester comprising an optionally substituted aliphatic or alkyl group (e.g., an aliphatic or alkyl comprising about 3 to about 30 carbons). In a particular embodiment, the aliphatic or alkyl group is the alkyl chain of a fatty acid or a saturated linear aliphatic chain, optionally substituted with at least one heteroatom. In a particular embodiment, the integrase inhibitor is selected from the group consisting of cabotegravir (CAB), raltegravir (RAL), elvitegravir (EVG), dolutegravir (DTG), and bictegravir (BIC). Compositions comprising at least one prodrug of the instant invention and at least one pharmaceutically acceptable carrier are also encompassed by the present invention.

In accordance with another aspect of the instant invention, nanoparticles comprising at least one prodrug of the instant invention and at least one polymer or surfactant are provided. In a particular embodiment, the prodrug is crystalline. In a particular embodiment, the polymer or surfactant is an amphiphilic block copolymer such as an amphiphilic block copolymer comprising at least one block of poly(oxyethylene) and at least one block of poly(oxypropylene) (e.g., poloxamer 407). The nanoparticle may comprise a polymer or surfactant linked to at least one targeting ligand. An individual nanoparticle may comprise targeted and non-targeted surfactants. In a particular embodiment, the nanoparticles have a diameter of about 100 nm to 1 μm. Compositions comprising at least one nanoparticle of the instant invention and at least one pharmaceutically acceptable carrier are also encompassed by the present invention.

In accordance with another aspect of the instant invention, methods for treating, inhibiting, and/or preventing a disease or disorder in a subject in need thereof are provided. The methods comprise administering to the subject at least one prodrug or nanoparticle of the instant invention, optionally within a composition comprising a pharmaceutically acceptable carrier. In a particular embodiment, the disease or disorder is a viral infection (e.g., a retroviral infection). In a particular embodiment, the method further comprises administering at least one further therapeutic agent or therapy for the disease or disorder, e.g., at least one additional anti-HIV compound.

BRIEF DESCRIPTIONS OF THE DRAWING

FIG. 1 provides a schematic of the synthesis of certain prodrugs of the instant invention.

Figure 2A:
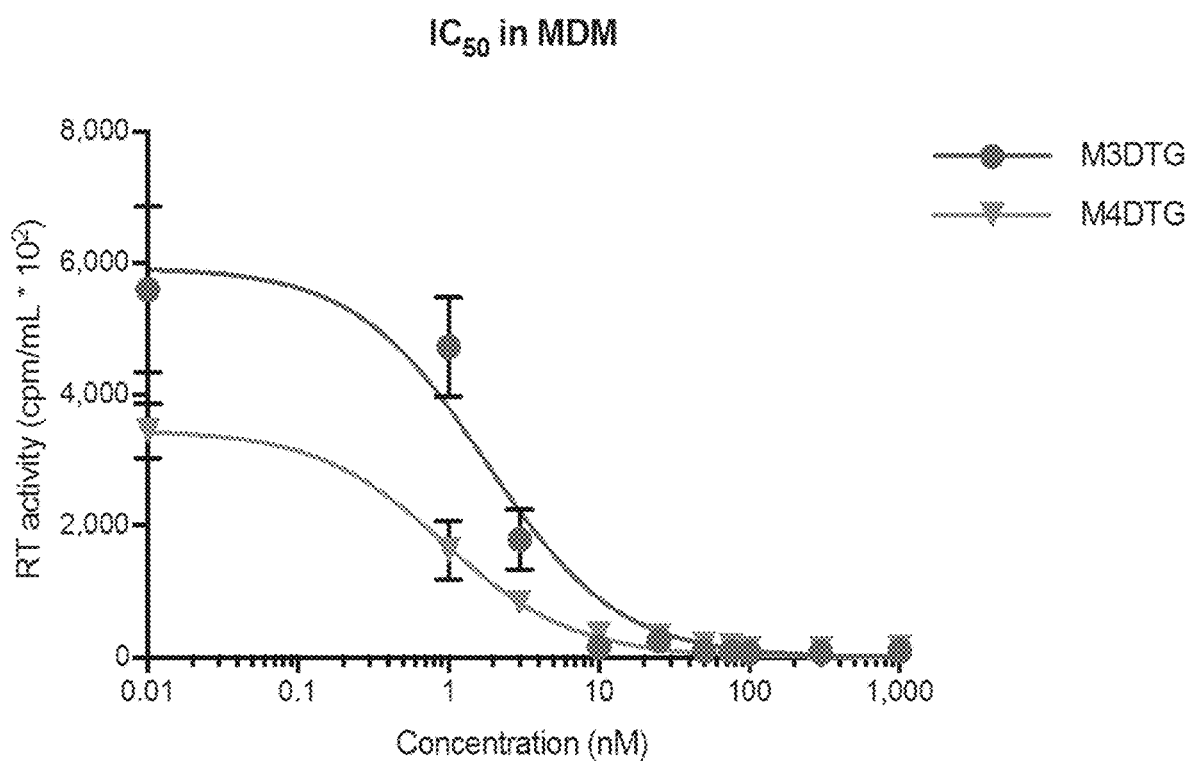
Figure 2B:
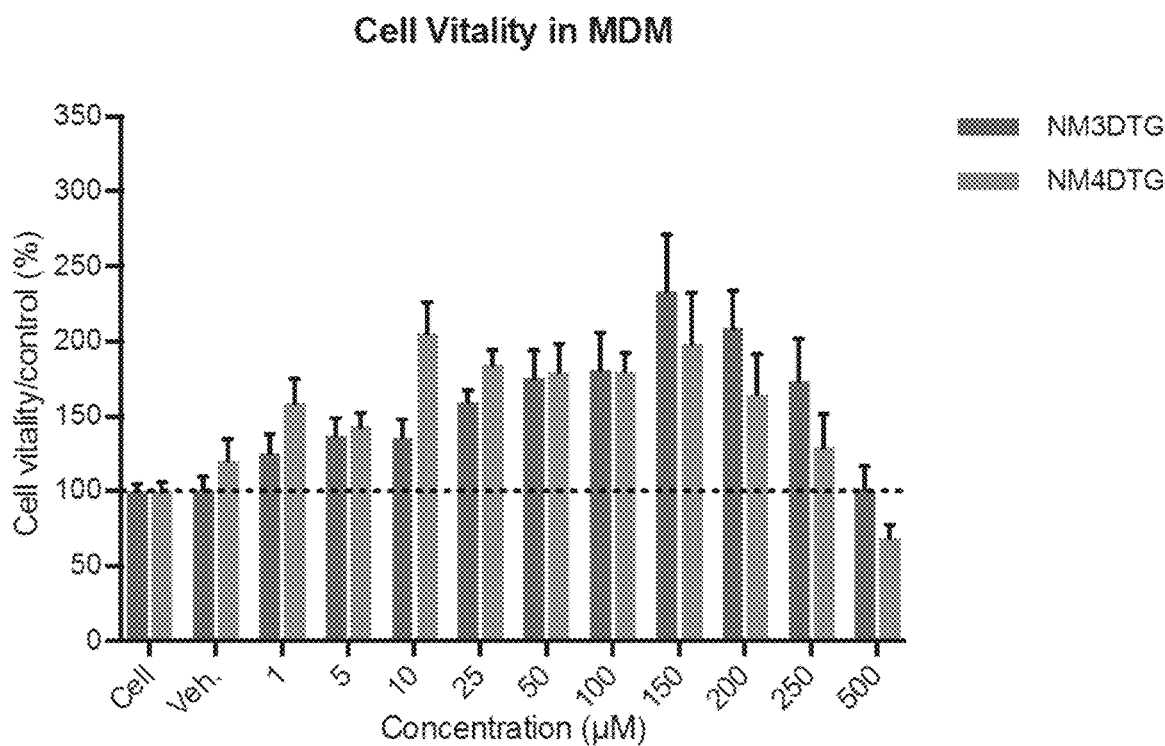

FIG. 2A provides a graph of HIV-1 reverse transcriptase (RT) activity in human monocyte derived macrophages (MDM) treated with the indicated concentration of drug and challenged with HIV-1$_{ADA}$. FIG. 2B provides a graph of the cell viability of MDM after nanoparticle (NM3DTG or NM4DTG) treatment at the indicated concentrations. Results were normalized to untreated control cells.

Figure 3A:
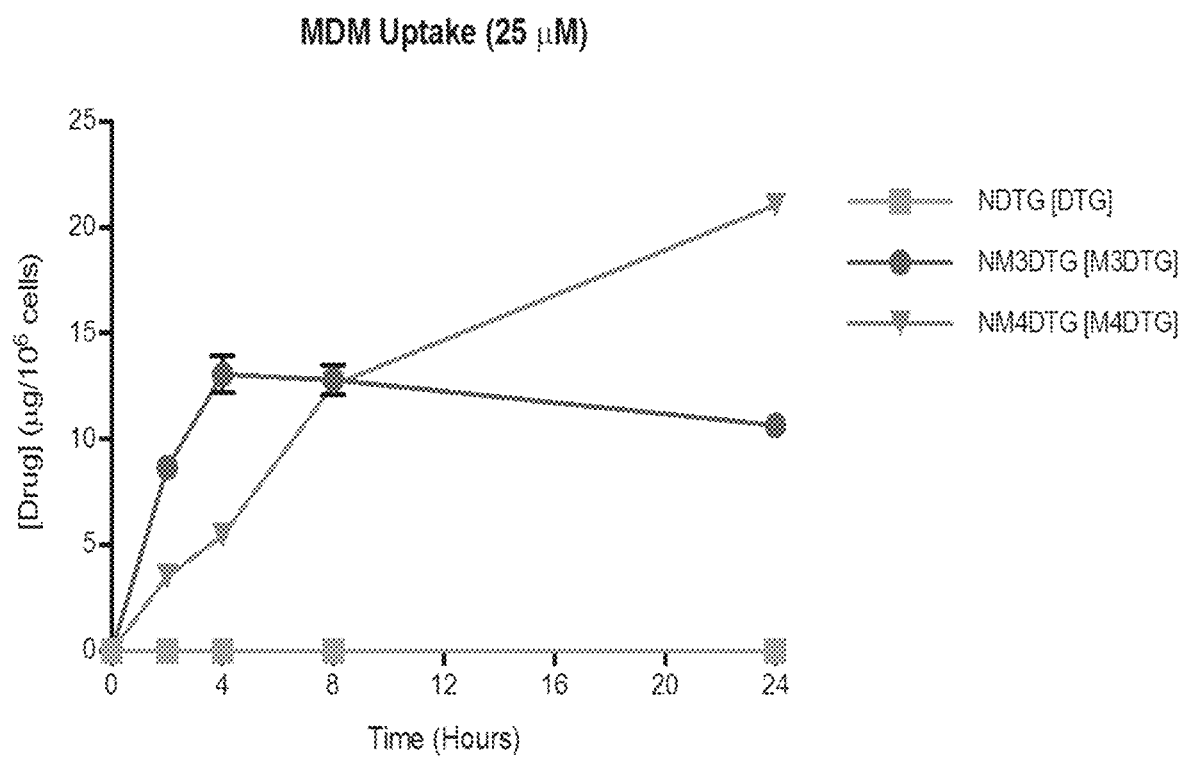
Figure 3B:
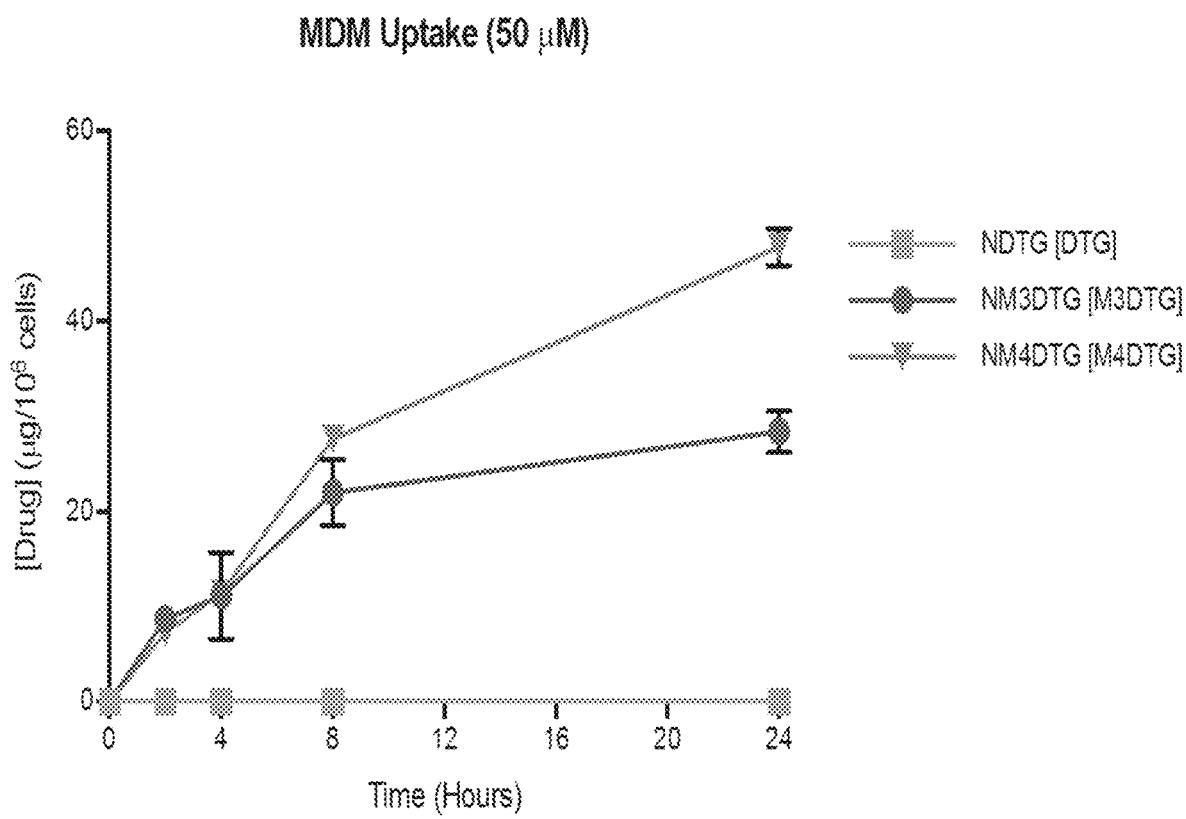

FIGS. 3A and 3B provide graphs of the drug uptake by MDM over a 24 hour period with equal drug concentrations at 25 μM (FIG. 3A) or 50 μM (FIG. 3B).

Figure 4A:
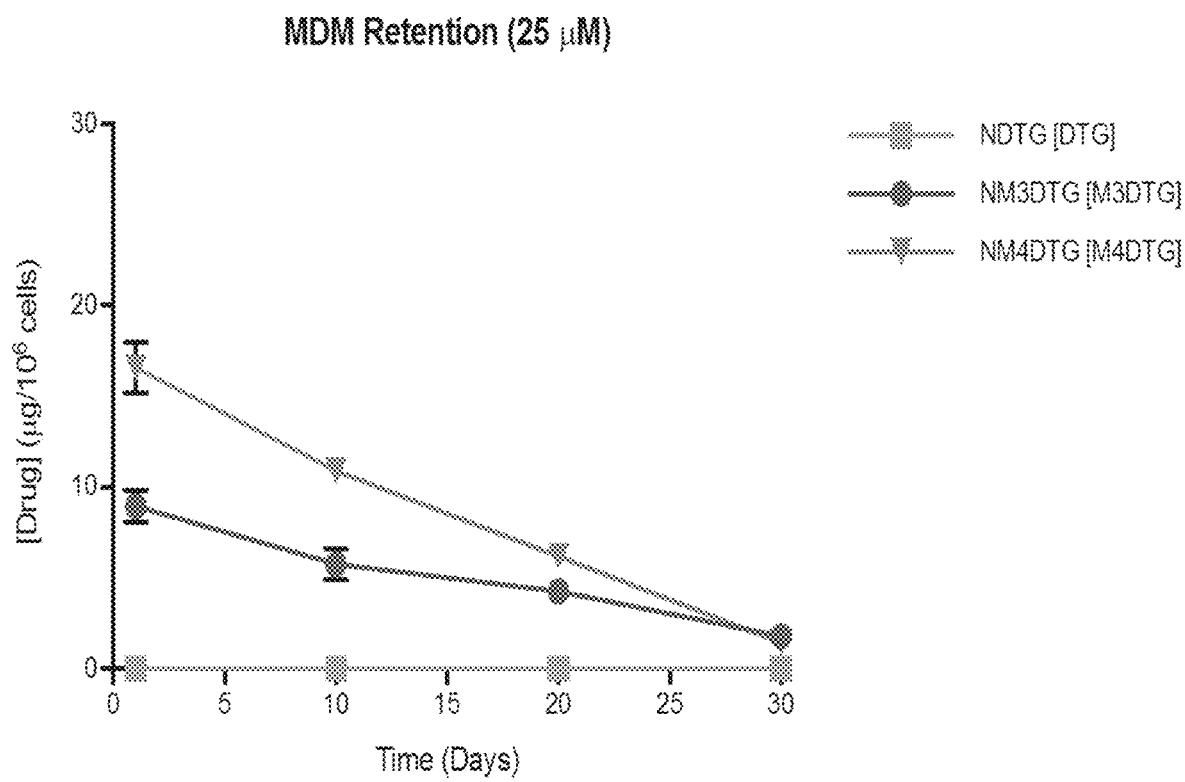
Figure 4B:
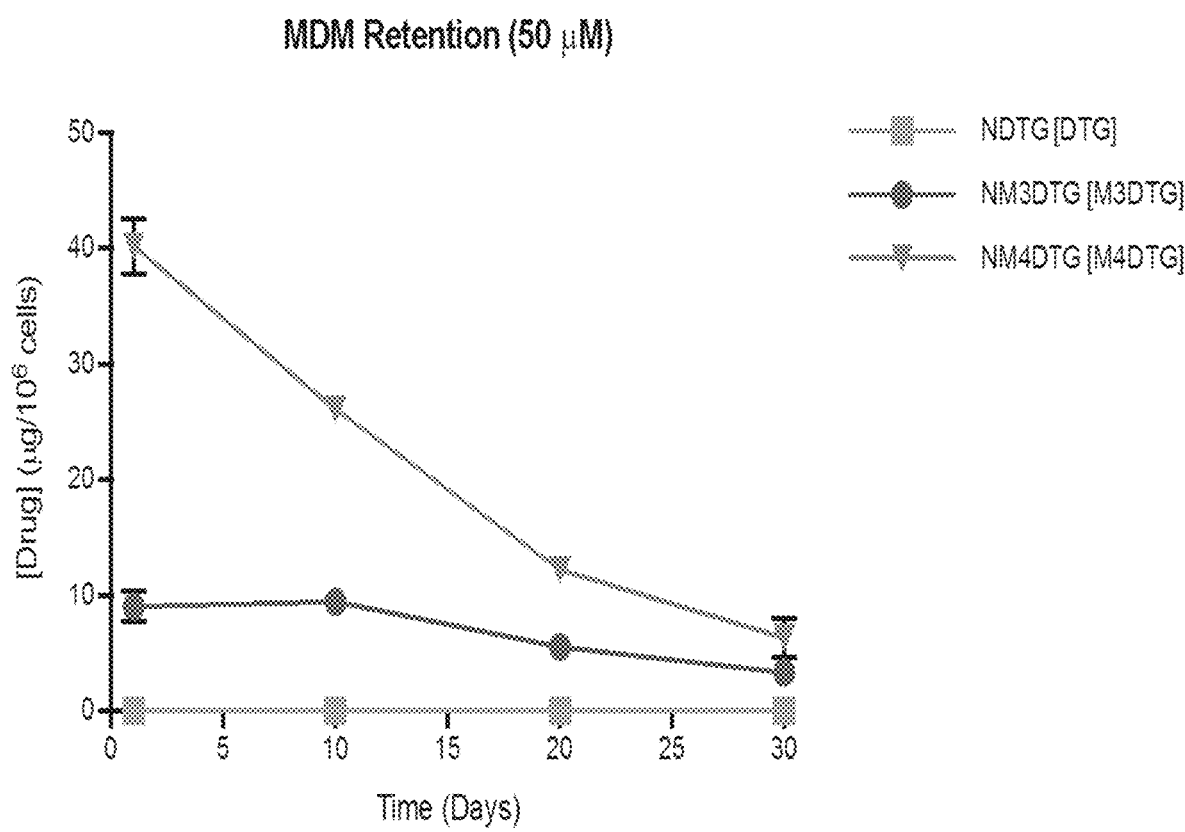

FIGS. 4A and 4B provide graphs of the drug retention by MDM over a 30 day period with equal drug concentrations at 25 μM (FIG. 4A) or 50 μM (FIG. 4B).

Figure 5A:
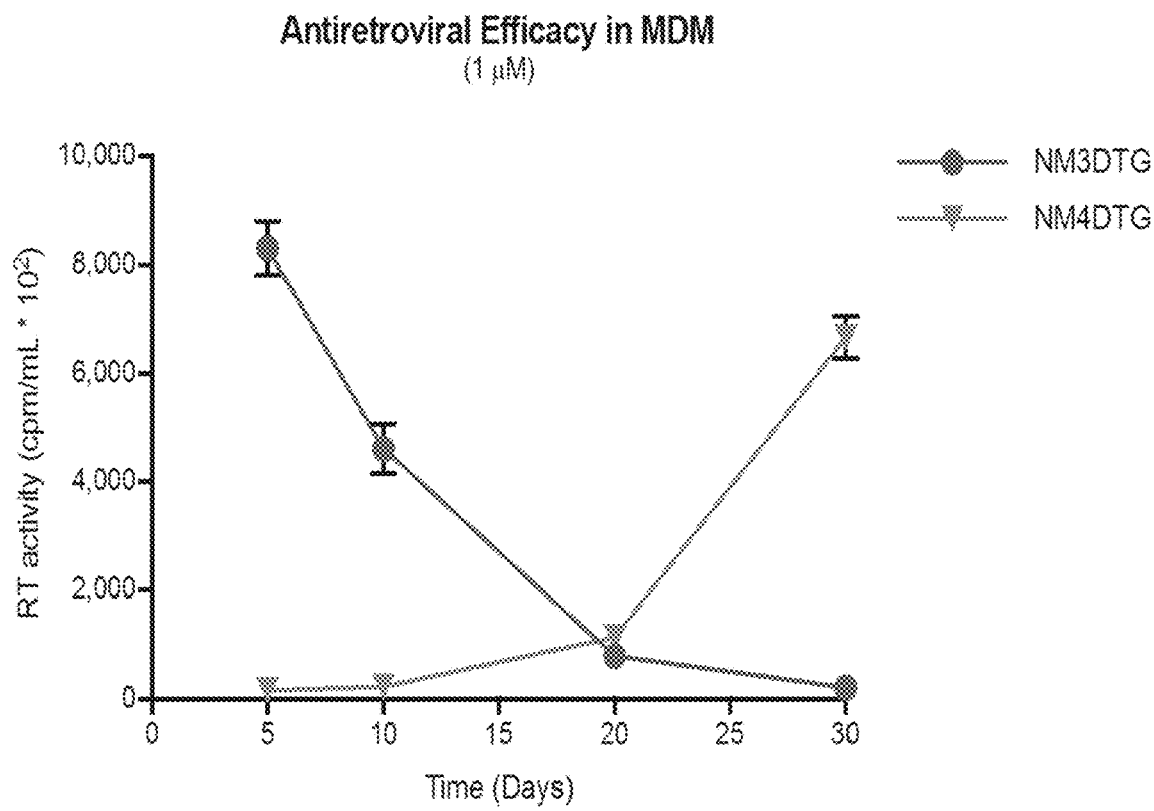
Figure 5B:
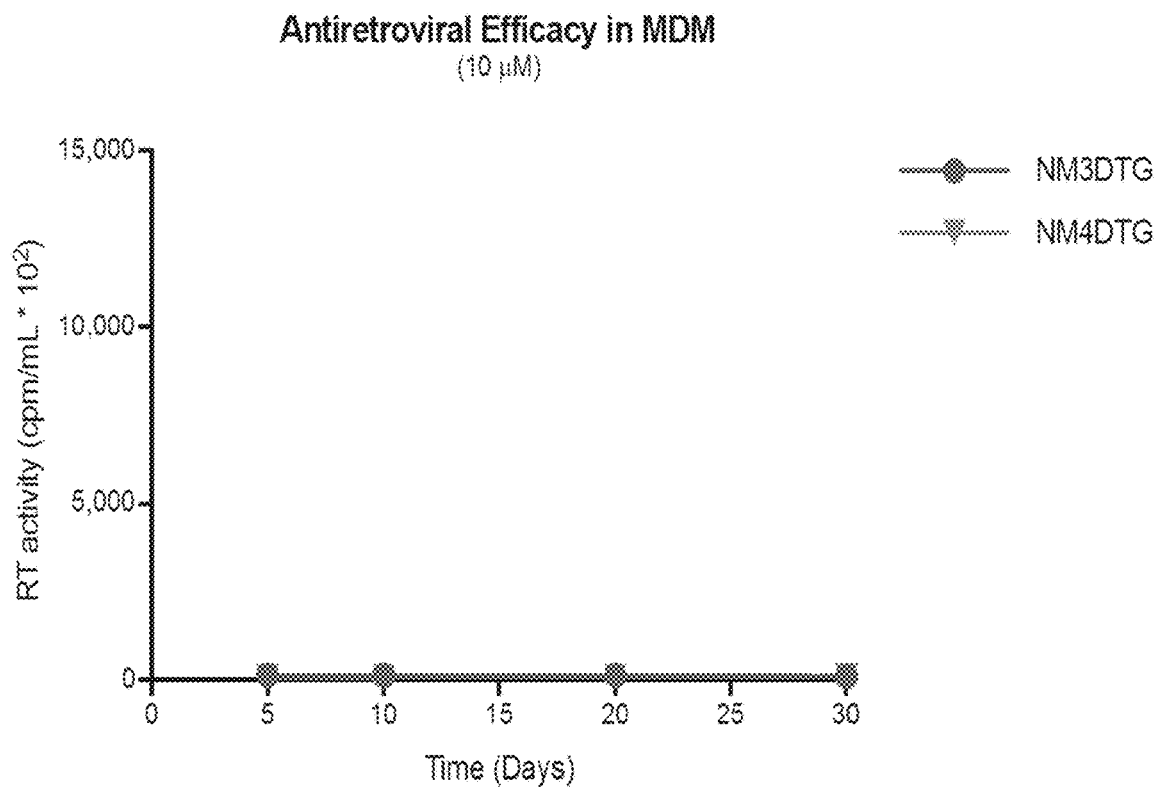

FIGS. 5A and 5B provide graphs of HIV-1 reverse transcriptase activity at the indicated timepoints in MDM treated with the indicated nanoparticles and challenged with HIV-1$_{ADA}$. MDM were pretreated for 8 hours with equal drug concentrations of 1 μM (FIG. 5A) or 10 μM (FIG. 5B) NM3DTG or NM4DTG. At the indicated times, cells were challenged with HIV-1$_{ADA}$ and media was collected after an additional 10 days and assayed for HIV-1 RT activity.

Figure 6A:
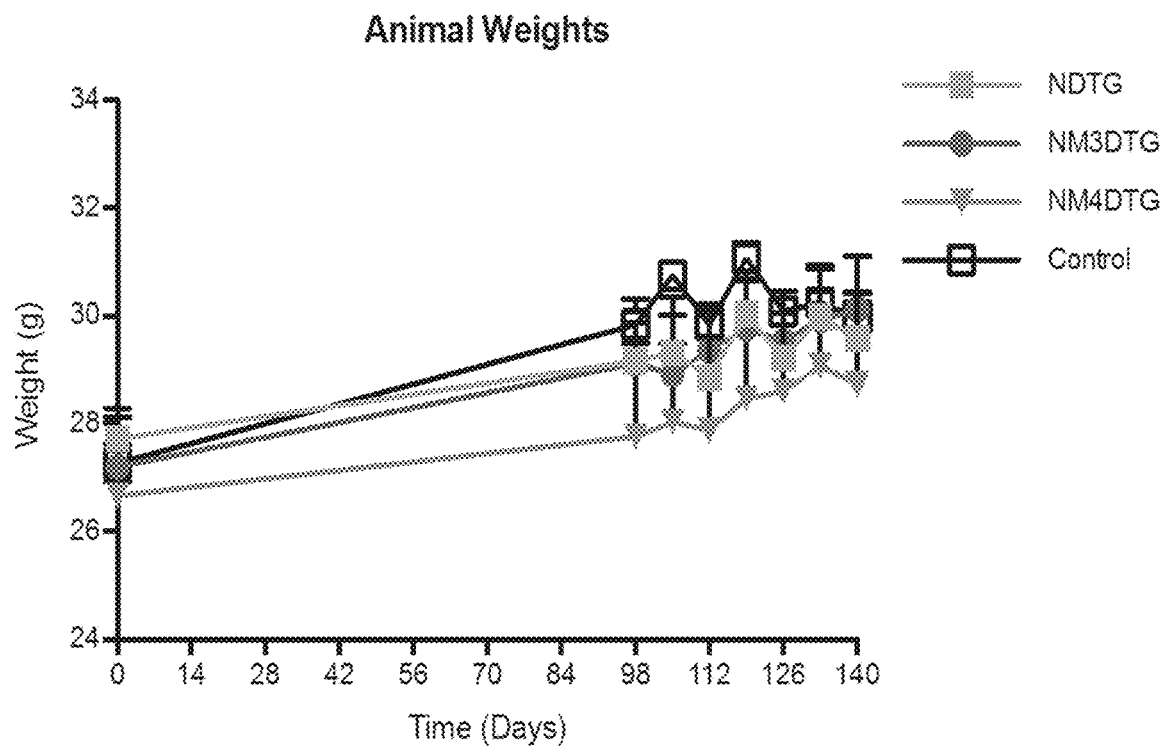
Figure 6B:
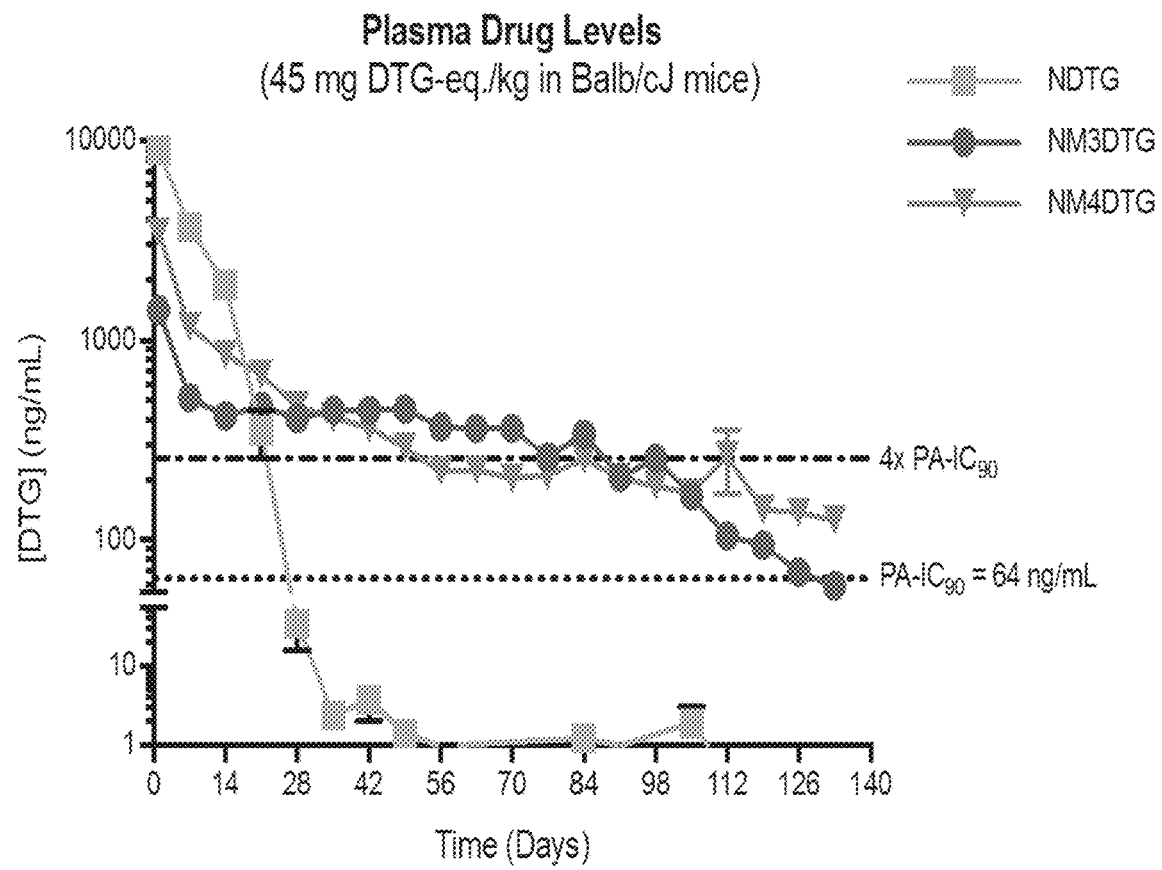

FIG. 6A provides a graph of weight of the mice during the pharmacokinetic studies. FIG. 6B provides a graph of plasma DTG levels after a single intramuscular (IM) dose of NDTG, NM3DTG, or NM4DTG in Balb/cJ mice. Administered dose was 45 mg DTG equivalents (eq)/kg. Top bold dashed line indicates plasma DTG 4×PA-IC$_{90}$ of 256 ng/ml and the bottom stippled line shows the plasma DTG PA-IC$_{90}$ of 64 ng/ml. n=3-5 animals/group.

DETAILED DESCRIPTION OF THE INVENTION

Maximal restriction of viral load in tissue infectious sites can facilitate viral eradication strategies. This can be achieved by generation of potent lipophilic and hydrophobic antiretroviral prodrug nanocrystals stabilized by surfactants. Hydrophobicities, drug hydrolysis rates, and antiretroviral potencies must be balanced for optimal therapeutic effect. Herein, dimer prodrugs and amino acid fatty ester prodrugs are shown to optimize therapeutic efficacy, particularly with regard to long acting slow effective release antiretroviral therapy (LASER ART). LASER ART refers to a long acting antiretroviral drug generated from a nanocrystal prodrug. Herein, it is shown that dimer prodrugs and amino acid fatty ester prodrugs unexpectedly serve to enhance DTG lipophilicity and hydrophobicity, improve drug potency, and slow prodrug hydrolysis, thereby extensively extending the half-life of the parent drug. The novel prodrugs enhance drug encapsulation with appropriate excipients and stabilizers, such as poloxamer 407 (P407). The nanoformulations provide sustained drug release and site specific antiretroviral drug delivery. The prodrugs comprise native drug conjugated to hydrophobic moieties via hydrolyzable covalent bonds. The nanoformulations of the prodrugs of the instant invention were readily taken up by human monocyte-derived macrophages (MDM) with sustained drug retention for 30 days in vitro; whereas parent drug nanoformulation showed rapid HIV-1 breakthrough in MDM. Notably, MDM treated with nanoformulations of the prodrugs of the instant invention exhibited sustained antiretroviral activities following HIV-1 challenge for up to 30 days after single drug treatment. Further, a single intramuscular (IM) injection of nanoformulations of the prodrugs of the instant invention at 45 mg DTG equivalents/kg into mice demonstrated a zero order controlled release kinetics of active DTG and provided drug levels at or above 4 times the PA-IC$_{90}$ for greater than several months. The nanoformulations presented herein improves upon current combination ART regimens that require multiple daily administrations by reducing pill burden, lowering the risk of viral rebound, limiting toxicities, and/or allowing for drug penetration into viral reservoirs.

Importantly, the nanoformulations also facilitate a dosing interval of once every three to six months (or even less frequently) to maximize the effectiveness of pre-exposure prophylaxis or treatment regimens.

Long acting slow effective release ART (LASER ART) formulations can extend dosing intervals, reduce systemic toxicity, and improve pharmacokinetic (PK) and pharmacodynamic (PD) profiles (Sillman, et al., Nat. Commun. (2018) 9:443; Zhou, et al., Biomaterials (2018) 151:53-65; McMillan, et al., Antimicrob. Agents Chemother. (2018) 62:e01316-17). Herein, novel integrase inhibitor prodrugs, long-acting slow effective release formulations thereof, and methods of synthesis and use thereof are provided. Integrase inhibitors (integrase strand transfer inhibitors (INSTIs)) are a class of antiretroviral drug designed to block the action of integrase (e.g., HIV integrase), a viral enzyme that inserts the viral genome into the DNA of the host cell. Examples of integrase inhibitors include, without limitation, cabotegravir (CAB, GSK1265744), raltegravir (RAL), elvitegravir (EVG), dolutegravir (DTG, GSK1349572), bictegravir (BIC, GS-9883), BI 224436 (Boehringer Ingelheim, Ingelheim, Germany), and MK-2048 (Merck, Kenilworth, NJ). The prodrugs of the instant invention and their slow effective release formulations exhibit enhanced potency and efficacy, increased cellular and tissue penetration and extended half-lives compared to parent integrase inhibitor. The prodrugs and their formulations of the instant invention and their combinations can be used in the management of viral (e.g., retroviral) infections.

Treatments of viral infections, particularly HIV infections, which are currently available, include inhibitors of viral entry, nucleoside reverse transcriptase, nucleotide reverse transcriptase, integrase, and protease. Resistance is linked to a shortened drug half-life, the viral life cycle, and rapid mutations resulting in a high genetic variability. Combination therapies, e.g., antiretroviral therapies (ART), which are considered "cocktail" therapy, have gained substantial attention. Benefits include decreased viral resistance, limited toxicities, improved adherence to therapeutic regimens and sustained antiretroviral efficacy. Combination therapies minimize potential drug resistance by suppressing viral (e.g., HIV) replication, thereby reducing spontaneous resistant mutants. Treatment failure is attributed, in part, to the short drug half-lives. Furthermore, failure can also be attributed, in part, to limited drug access to tissue and cellular viral reservoirs, thereby precluding viral eradication efforts. To these ends, the development of cell and tissue targeted nanoformulated prodrug (nanoparticle) platforms are of considerable interest in the management of viral (e.g., HIV) infections. Pre-exposure prophylaxis (PrEP) is another strategy used in the management of viral (e.g., HIV) transmission. For example, TRUVADA® (tenofovir/emtricitabine) has been approved for pre-exposure prophylaxis against HIV infection. Additionally, the combination of lamivudine and zidovudine (COMBIVIR®) has been used as pre-exposure prophylaxis and post-exposure prophylaxis.

The prodrugs and nanoformulated prodrugs (nanoparticles) provided herein unexpectedly extend the drug half-life, increase hydrophobicity and lipophilicity, and improve antiretroviral efficacy. This will benefit people who have to receive daily high doses or even several doses a day, since lower dosage with less dosing frequency would not only decrease the side effects, but also be convenient to the patients. The prodrugs and nanoformulated prodrugs (nanoparticles) provided herein may also be used as a post-exposure treatment and/or pre-exposure prophylaxis (e.g., for people who are at high risk of contracting HIV-1). In other words, the prodrugs and nanoparticles of the instant invention and their combination may be used to prevent a viral infection (e.g., HIV infection) and/or treat or inhibit an acute or long term viral infection (e.g., HIV infection). While the prodrugs and nanoparticles of the instant invention are generally described as anti-HIV agents, the prodrugs and nanoformulations of the instant invention are also effective against other viral infections including, without limitation: retroviruses (e.g., lentiviruses), hepatitis B virus (HBV), hepatitis C virus (HCV), and human T-cell leukemia viruses (HTLV), particularly retroviruses.

The present invention describes novel, potent, broad spectrum prodrugs with improved biological activity over parent drugs. Methods for the encapsulation of the prodrugs into long acting slow effective formulations for efficient intracellular and tissue delivery and extended drug half-lives are also provided. The long acting slow effective release (LASER) compositions described herein exhibit enhanced potency and may be used as effective therapeutic or preventative interventions against viral infections (e.g., retroviral infections).

Prodrugs of the instant invention allow for the efficient intracellular delivery of integrase inhibitors. Herein, prodrugs are provided which are derivatives of integrase inhibitors. In certain embodiments, a chemical moiety of the integrase inhibitor, particularly an oxygen containing moiety such as a hydroxyl group, has been replaced with an ester moiety (e.g., an ester moiety comprising a hydrophobic and lipophilic cleavable moiety). Prodrugs of the instant invention include, but are not limited to: fatty diester and monoester prodrugs, fatty ester integrase inhibitor dimer prodrugs, and amino acid fatty esters.

As described herein, the prodrugs can improve drug potency, accelerate intracellular and tissue penetrance, protein binding, and bioavailability. The hydrophobic nature of the synthesized prodrugs facilitates encapsulation into long acting slow release drug nanocrystals with improved biopharmaceutical features. The nanoformulations of the instant invention may be composed of prodrug particles dispersed in sterile aqueous suspensions and stabilized by polymeric excipients, lipids, and/or surfactants or polymers. Without being bound by theory, the mechanism of drug release involves dissolution of the prodrug from the nanoparticle followed by efficient cleavage to generate bioactive agents, e.g., an integrase inhibitor and/or a broad-spectrum antiviral fatty alcohol.

The benefits of the system described herein include, without limitation, improved drug potency, bioavailability and extended half-life for patient convenience. Indeed, the nanoformulations described in this invention displayed significant increase in drug uptake by monocyte-derived macrophages (MDM). Also, the modified drug and nanoparticles exhibited enhanced potency through increased and extended inhibition of viral replication. Therefore, the nanoformulations of the instant invention allow for enhancement of antiviral potency and accelerated drug delivery to anatomical reservoirs of infection.

In accordance with the instant invention, prodrugs of integrase inhibitors are provided. In a particular embodiment, the integrase inhibitor is selected from the group consisting of cabotegravir (CAB), raltegravir (RAL), elvitegravir (EVG), dolutegravir (DTG), bictegravir (BIC), BI 224436, and MK-2048. In a particular embodiment, the integrase inhibitor is selected from the group consisting of cabotegravir (CAB), raltegravir (RAL), elvitegravir (EVG), dolutegravir (DTG), and bictegravir (BIC). In a particular embodiment, the integrase inhibitor is dolutegravir (DTG).

In a particular embodiment, the integrase inhibitor is cabotegravir (CAB). Examples of the chemical structures of these integrase inhibitors are:

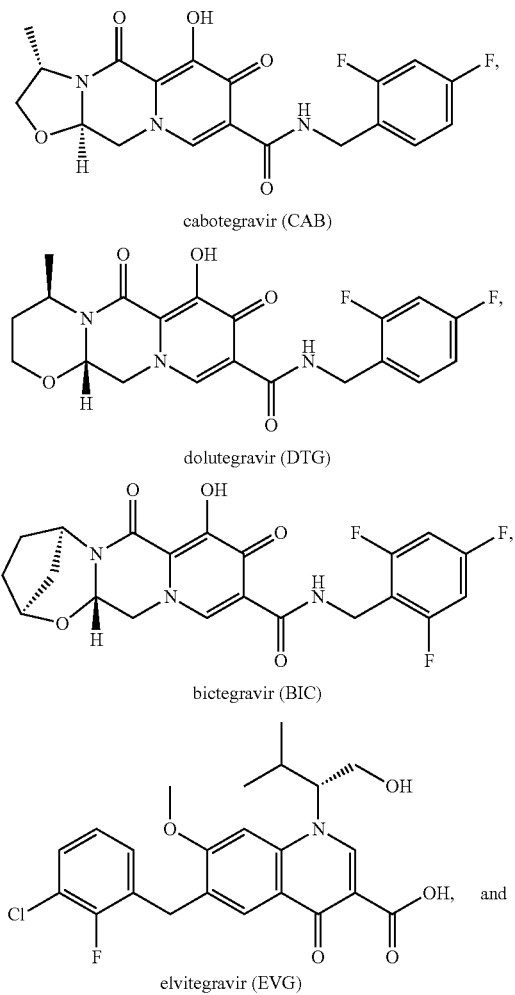

cabotegravir (CAB)

dolutegravir (DTG)

bictegravir (BIC)

elvitegravir (EVG)

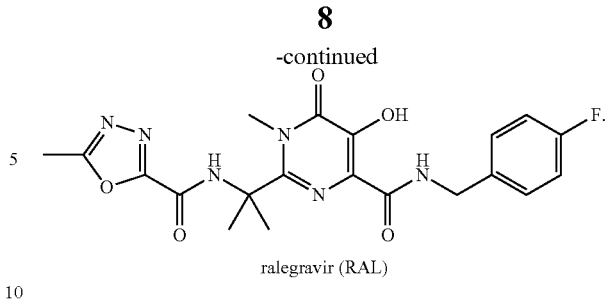

ralegravir (RAL)

In some embodiments, the prodrug of the present invention is a dimer of two integrase inhibitors that are connected by a linker. The integrase inhibitors in the dimer prodrug may be the same integrase inhibitor or they may be different integrase inhibitors. In a particular embodiment, the prodrug comprises an integrase inhibitor wherein a chemical moiety, particularly an oxygen containing moiety such as a hydroxyl group, is replaced with an ester comprising the linker. In a particular embodiment, the linker is an optionally substituted aliphatic or alkyl group. The aliphatic or alkyl group may be unsaturated or saturated, and may be substituted with at least one heteroatom (e.g., O, N, or S). In a particular embodiment, the alkyl or aliphatic group is hydrophobic. In a particular embodiment, the linker is an optionally substituted hydrocarbon chain, particularly saturated. In a particular embodiment, the linker a hydrocarbon chain. In a particular embodiment, the linker is a saturated linear aliphatic chain. In a particular embodiment, the alkyl or aliphatic group comprises about 1 to about 30 carbons (e.g., in the main chain of the alkyl or aliphatic group), which may be substituted with at least one heteroatom (e.g., O, N, or S). In a particular embodiment, the linker is 1 to about 30 carbon atoms in length, 1 to about 28 carbons in length, 1 to about 26 carbons in length, 1 to about 24 carbons in length, 1 to about 22 carbons in length, 1 to about 20 carbons in length, 1 to about 18 carbons in length, 1 to about 16 carbons in length, 1 to about 10 carbons in length, 10 to about 22 carbons in length, 10 to about 20 carbons in length, 12 to about 20 carbons in length, 14 to about 18 carbons in length, or about 16 carbons in length. Numbering here excludes the carbon in the C=O of the ester.

In a particular embodiment, the prodrug of the instant invention is selected from the following group or a pharmaceutically acceptable salt or stereoisomer thereof:

(I)

(II)

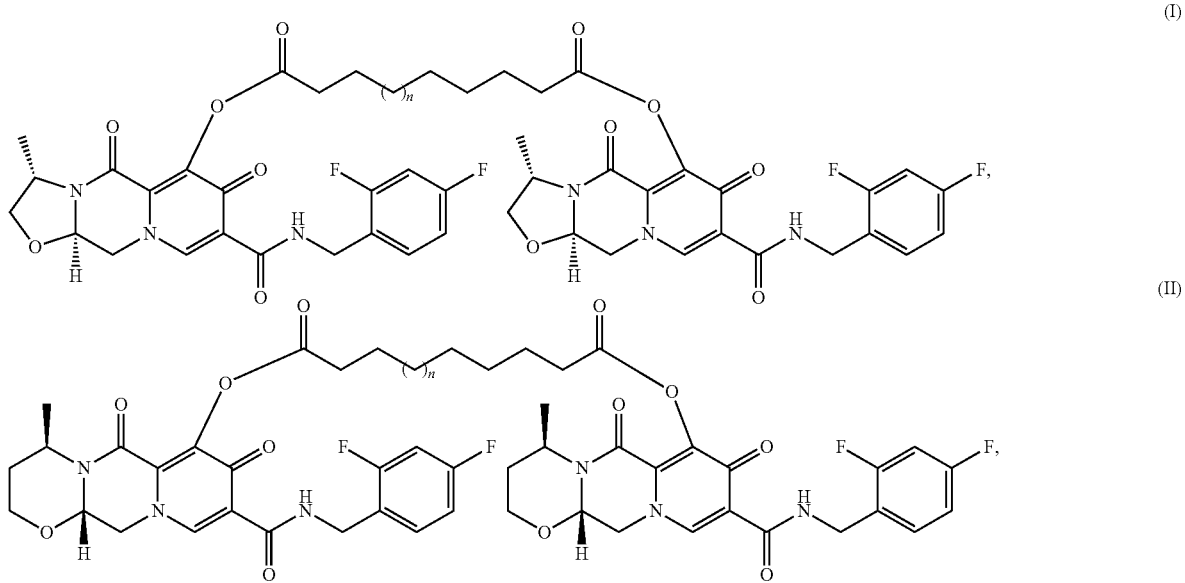

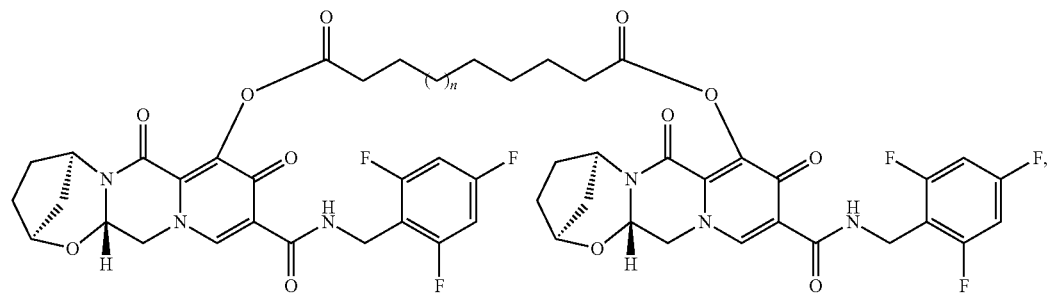

(III)

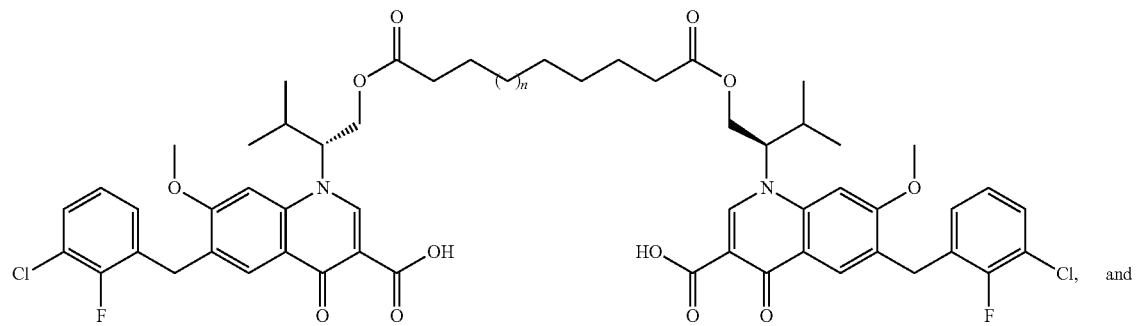

(IV)

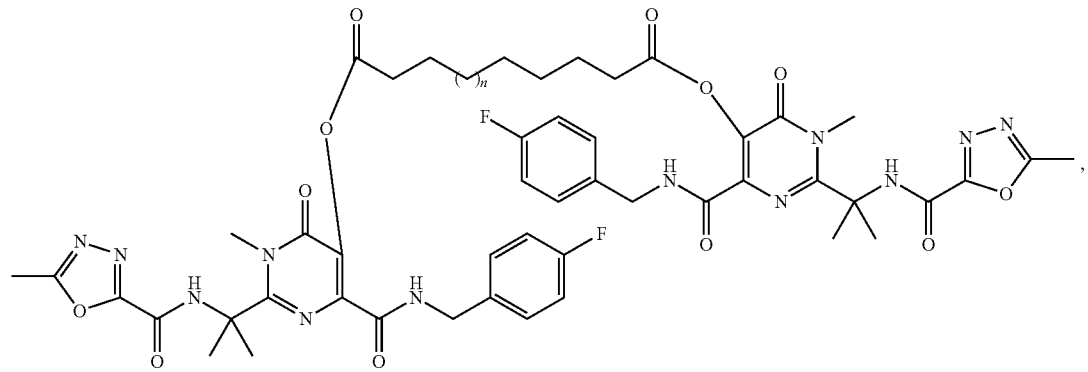

(V)

wherein n is from 1 to about 24, 1 to about 22, 1 to about 20, 1 to about 18, 1 to about 16, 1 to about 14, 1 to about 12, 1 to about 10, 1 to about 4, 4 to about 16, 4 to about 14, 6 to about 14, 8 to about 12, or about 10. In a particular embodiment, the linker may be substituted with at least one heteroatom (e.g., O, N, or S).

In a particular embodiment, the prodrug of the instant invention is:

(M3DTG) or a pharmaceutically acceptable salt or stereoisomer thereof. In a particular embodiment, the one or both of the DTG is replaced with CAB. In a particular embodiment, the prodrug is M3CAB or M4CAB, or a pharmaceutically acceptable salt or stereoisomer thereof.

In some embodiments, the prodrug of the present invention is an amino acid fatty ester. In a particular embodiment, the prodrug comprises an integrase inhibitor wherein a chemical moiety, particularly an oxygen containing moiety

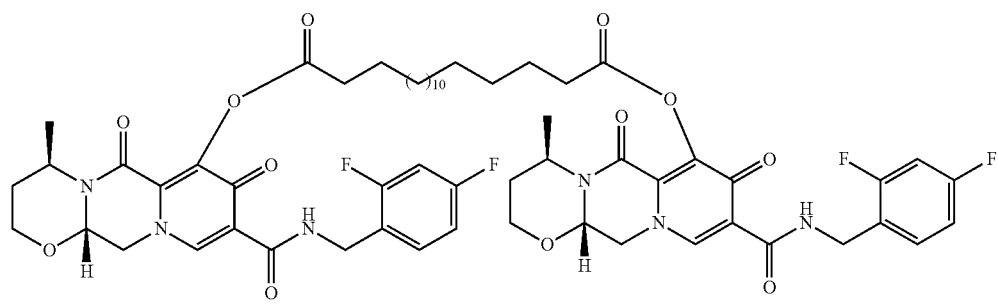

such as a hydroxyl group, is replaced with an amino acid fatty ester. The amino acid fatty ester may contain one or more amino acids, residues or side chains. In a particular embodiment, the amino fatty ester comprises 1 to 10 amino acids, particularly 1 to 7 amino acids, 1 to 5 amino acids, 1 to 4 amino acids, 1 to 3 amino acids, 1 to 2 amino acids, or 1 amino acid. In a particular embodiment, the amino fatty ester comprises only one amino acid, residue, or side chain. In a particular embodiment, the amino acid forms an amide bond with the C=O of the ester. In a particular embodiment, the prodrug comprises an integrase inhibitor wherein a hydroxyl group is replaced with the O of the amino acid carboxyl (—COOH) group. Any amino acid may be used. The amino acids of the amino acid fatty ester may be the same or different. In a particular embodiment, the amino acid is not charged (e.g., not aspartic acid, glutamic acid, arginine, lysine, or histidine). In a particular embodiment, the amino acid is hydrophobic. In a particular embodiment, the amino acid is selected from the group consisting of glycine, alanine, valine, leucine, isoleucine, proline, phenylalanine, methionine, and tryptophan. In a particular embodiment, the amino acid is selected from the group consisting of alanine, valine, phenylalanine, proline, tyrosine, and lysine. In a particular embodiment, the amino acid is proline. In a particular embodiment, the amino acid fatty ester comprises a hydrophobic and lipophilic cleavable moiety (e.g., therapeutic fatty alcohols). The hydrophobic and lipophilic cleavable moiety (e.g., therapeutic fatty alcohols) can exhibit antiviral activity against enveloped viruses (Katz, et al., Ann. NY Acad. Sci. (1994) 724:472-88). Notably, synergistic interactions between therapeutic fatty alcohols and nucleoside analogs can substantially enhance antiviral potency of the nucleosides (Marcelletti, et al., Antiviral Res. (2002) 56:153-66).

The hydrophobic nature of the synthesized prodrugs facilitates encapsulation into long acting slow release drug nanocrystals with improved biopharmaceutical features. The nanoformulations of the instant invention may be composed of prodrug particles dispersed in sterile aqueous suspensions and stabilized by polymeric excipients, lipids, and/or surfactants or polymers. Without being bound by theory, the mechanism of drug release involves dissolution of the prodrug from the nanoparticle followed by efficient cleavage to generate two bioactive agents, i.e., the integrase inhibitor and the broad-spectrum antiviral fatty alcohols.

In a particular embodiment, the prodrug of the instant invention is selected from the following group or a pharmaceutically acceptable salt or stereoisomer thereof:

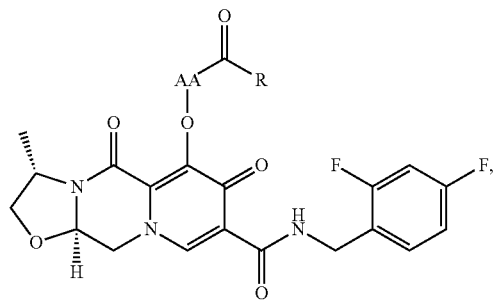

(VI)

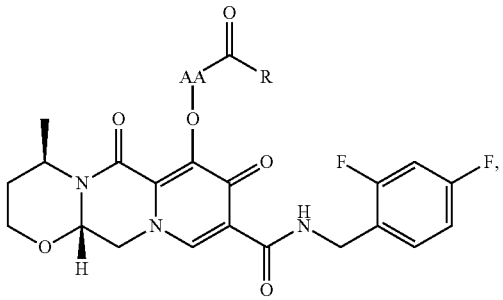

(VII)

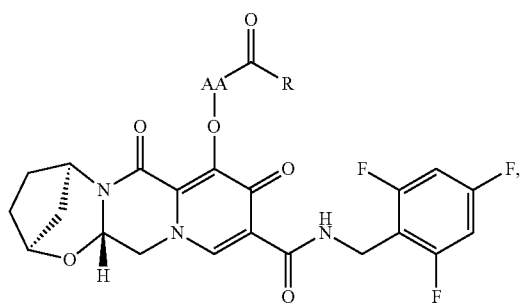

(VIII)

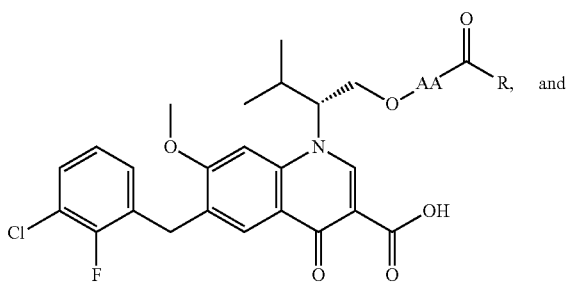

(IX)

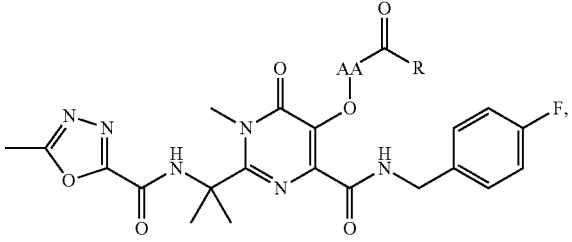

(X)

wherein R is an optionally substituted aliphatic or alkyl, and wherein AA is one or more amino acids, residues, or side chains. In a particular embodiment, the O attached to AA in the above formulas is the O of the hydroxyl in the amino acid carboxyl (—COOH) group. In a particular embodiment, the amino acid forms an amide bond. In a particular embodiment, the amino fatty ester comprises 1 to 10 amino acids, particularly 1 to 7 amino acids, 1 to 5 amino acids, 1 to 4 amino acids, 1 to 3 amino acids, 1 to 2 amino acids, or 1 amino acid. In a particular embodiment, the amino fatty ester comprises only one amino acid. Any amino acid may be used. The amino acids of the amino acid fatty ester may be the same or different. In a particular embodiment, the amino acid is not charged (e.g., not aspartic acid, glutamic acid, arginine, lysine, or histidine). In a particular embodiment, the amino acid is hydrophobic. In a particular embodiment, the amino acid is selected from the group consisting of alanine, valine, phenylalanine, proline, tyrosine, and lysine.

In a particular embodiment, R is the side chain of a fatty acid. The aliphatic or alkyl group may be unsaturated or saturated, and may be substituted with at least one heteroatom (e.g., O, N, or S). In a particular embodiment, R may contain an aromatic moiety that may be substituted with at least one heteroatom (e.g., O, N, or S). In a particular embodiment, R has between 1 and 24 carbons. In a particular embodiment, R has between 10 and 24 carbons.

In a particular embodiment, the alkyl or aliphatic group is hydrophobic. In a particular embodiment, R is an optionally substituted hydrocarbon chain, particularly saturated. In a particular embodiment, R is a saturated linear aliphatic chain. In a particular embodiment, the alkyl or aliphatic group comprises about 1 to about 30 carbons, about 1 to about 24 carbons, or about 10 to about 24 carbons (e.g., in the main chain of the alkyl or aliphatic group), which may be substituted with at least one heteroatom (e.g., O, N, or S). In a particular embodiment, R is a C1-C29 unsaturated or saturated alkyl or aliphatic group, which may be substituted with at least one heteroatom (e.g., O, N, or S). In a particular embodiment, R is a C1-C21 unsaturated or saturated alkyl or aliphatic group, which may be substituted with at least one heteroatom (e.g., O, N, or S). In a particular embodiment, R is a C9-C29 unsaturated or saturated alkyl or aliphatic group, which may be substituted with at least one heteroatom (e.g., O, N, or S). In a particular embodiment, R is a C9-C21 unsaturated or saturated alkyl or aliphatic group, which may be substituted with at least one heteroatom (e.g., O, N, or S). In a particular embodiment, R is a C7-C23 unsaturated or saturated alkyl or aliphatic group, which may be substituted with at least one heteroatom (e.g., O, N, or S). In a particular embodiment, R is a C9-C21 unsaturated or saturated alkyl or aliphatic group, which may be substituted with at least one heteroatom (e.g., O, N, or S). In a particular embodiment, R is a C11-C19 unsaturated or saturated alkyl or aliphatic group, which may be substituted with at least one heteroatom (e.g., O, N, or S). In a particular embodiment, R is a C13-C19 unsaturated or saturated alkyl or aliphatic group, which may be substituted with at least one heteroatom (e.g., O, N, or S). In a particular embodiment, R is a C13-C17 unsaturated or saturated alkyl or aliphatic group, which may be substituted with at least one heteroatom (e.g., O, N, or S). In a particular embodiment, R is a C17 unsaturated or saturated alkyl or aliphatic group, which may be substituted with at least one heteroatom (e.g., O, N, or S). In a particular embodiment, R is a C15 unsaturated or saturated alkyl or aliphatic group, which may be substituted with at least one heteroatom (e.g., O, N, or S).

In a particular embodiment, R is the alkyl chain of a fatty acid (saturated or unsaturated), particularly a C4-C30 fatty acid, C6-C28 fatty acid, C8-C26 fatty acid a C10-C24 fatty acid, a C12-C22 fatty acid, a C14-C22 fatty acid, a C14-C20 fatty acid, a C14-C18 fatty acid, a C16-C18 fatty acid, a C18 fatty acid, or a C16 fatty acid (numbering here is inclusive of the carbon in the C═O of the ester).

In a particular embodiment, R is a saturated linear aliphatic chain or a hydrocarbon chain of at least 9 carbons (e.g., 9 to 21 carbons in length in the chain, 9 to 19 carbons in length in the chain, 11 to 17 carbons in length in the chain, 13 to 21 carbons in length in the chain, 13 to 19 carbons in length in the chain, 15 to 17 carbons in length in the chain, or 15 or 17 carbons in length in the chain). In a particular embodiment, R is a saturated linear aliphatic chain or a hydrocarbon chain of 12, 13, 14, 15, 16, 17, 18, 19, 20, or 21 carbons in length, particularly 12, 13, 14, 15, 16, 17, 18, or 19 carbons in length, 15, 16, or 17 carbons in length, or 15 carbons in length. In a particular embodiment, R is a saturated linear aliphatic chain or a hydrocarbon chain of 15 carbons in length.

In a particular embodiment, the prodrug of the instant invention is:

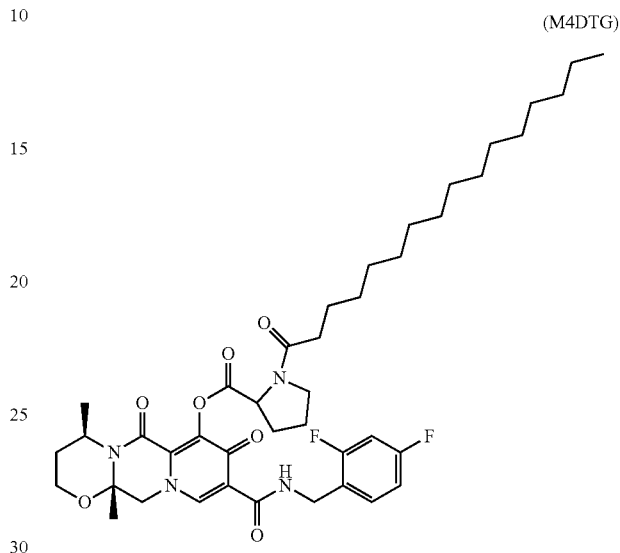

(M4DTG)

or a pharmaceutically acceptable salt or stereoisomer thereof. In a particular embodiment, the DTG is replaced with CAB. In a particular embodiment, the prodrug is M5CAB or M6CAB, or a pharmaceutically acceptable salt or stereoisomer thereof.

The instant invention also encompasses nanoparticles (sometimes referred to herein as nanoformulations) comprising the prodrug of the instant invention. The nanoparticles may be used for the delivery of the compounds to a cell or host (e.g., in vitro or in vivo). In a particular embodiment, the nanoparticle is used for the delivery of antiretroviral therapy to a subject. The nanoparticles of the instant invention comprise at least one prodrug and at least one surfactant or polymer. In a particular embodiment, the nanoparticles comprise a spectroscopic-defined surfactant/polymer:drug ratio that maintains optimal targeting of the drug nanoparticle to maintain a macrophage depot. These components of the nanoparticle, along with other optional components, are described hereinbelow.

Methods of synthesizing the nanoparticles of the instant invention are known in the art. In a particular embodiment, the methods generate nanoparticles comprising a prodrug (e.g., crystalline or amorphous) coated (either partially or completely) with a polymer and/or surfactant. Examples of synthesis methods include, without limitation, milling (e.g., wet milling), homogenization (e.g., high pressure homogenization), particle replication in nonwetting template (PRINT) technology, and/or sonication techniques. For example, U.S. Patent Application Publication No. 2013/0236553, incorporated by reference herein, provides methods suitable for synthesizing nanoparticles of the instant invention. In a particular embodiment, the polymers or surfactants are firstly chemically modified with targeting ligands and then used directly or mixed with non-targeted polymers or surfactants in certain molar ratios to coat on the surface of prodrug suspensions—e.g., by using a nanoparticle synthesis process (e.g., a crystalline nanoparticle synthesis process) such as milling (e.g., wet milling), homogenization (e.g., high pressure homogenization), particle replication in nonwetting template (PRINT) technology, and/or sonication techniques, thereby preparing targeted nanoformulations. The nanoparticles may be used with or without further purification, although the avoidance of further purification is desirable for quicker production of the nanoparticles. In a particular embodiment, the nanoparticles are synthesized using milling and/or homogenization. Targeted nanoparticles (e.g., using ligands (optionally with high molecular weight)) may be developed through either physically or chemically coating and/or binding on the surface of polymers or surfactants and/or drug nanosuspensions.

In a particular embodiment, the nanoparticles of the instant invention are synthesized by adding the prodrug (e.g., crystals) to a polymer or surfactant solution and then generating the nanoparticles (e.g., by wet milling or high pressure homogenization). The prodrug and polymer or surfactant solution may be agitated prior to the wet milling or high pressure homogenization.

The nanoparticles of the instant invention may be used to deliver at least one prodrug of the instant invention to a cell or a subject (including non-human animals). In a particular embodiment, the nanoparticle comprises more than one dimer prodrug (i.e., at least two unique dimer prodrugs). In a particular embodiment, the nanoparticle comprises more than one amino acid fatty ester prodrug (i.e., at least two unique amino acid fatty ester prodrugs). In a particular embodiment, the nanoparticle comprises at least one amino acid fatty ester prodrug and at least one dimer prodrug. The nanoparticles of the instant invention may further comprise at least one other agent or compound, particularly a bioactive agent, particularly a therapeutic agent (e.g., antiviral compound) or diagnostic agent, particularly at least one antiviral or antiretroviral. In a particular embodiment, the nanoparticles of the instant invention comprise at least two therapeutic agents, particularly wherein at least one is a prodrug of the instant invention. For example, the nanoparticle may comprise an integrase inhibitor prodrug of the instant invention and at least one other therapeutic agent (e.g., an anti-HIV agent).

In a particular embodiment, the nanoparticles of the instant invention are a submicron colloidal dispersion of nanosized prodrug crystals stabilized by polymers or surfactants (e.g., surfactant-coated drug crystals; a nanoformulation). In a particular embodiment, the prodrug may be crystalline (solids having the characteristics of crystals), amorphous, or are solid-state nanoparticles of the prodrug that is formed as crystal that combines the drug and polymer or surfactant. In a particular embodiment, the prodrug is crystalline. As used herein, the term "crystalline" refers to an ordered state (i.e., non-amorphous) and/or a substance exhibiting long-range order in three dimensions. In a particular embodiment, the majority (e.g., at least 50%, 60%, 70%, 80%, 90%, 95% or more) of the prodrug and, optionally, the hydrophobic portion of the surfactant or polymer are crystalline.

In a particular embodiment, the nanoparticle of the instant invention is up to about 2 or 3 µm in diameter (e.g., z-average diameter) or its longest dimension, particularly up to about 1 µm (e.g., about 100 nm to about 1 µm). For example, the diameter or longest dimension of the nanoparticle may be about 50 to about 800 nm. In a particular embodiment, the diameter or longest dimension of the nanoparticle is about 50 to about 750 nm, about 50 to about 600 nm, about 50 to about 500 nm, about 200 to about 600 nm, about 200 nm to about 500 nm, about 200 nm to about 400 nm, about 250 nm to about 350 nm, or about 250 nm to about 400 nm. The nanoparticles may be, for example, rod shaped, elongated rods, irregular, or round shaped. The nanoparticles of the instant invention may be neutral or charged. The nanoparticles may be charged positively or negatively.

As stated hereinabove, the nanoparticles of the instant invention comprise at least one polymer or surfactant. A "surfactant" refers to a surface-active agent, including substances commonly referred to as wetting agents, detergents, dispersing agents, or emulsifying agents. Surfactants are usually organic compounds that are amphiphilic.

Examples of polymers or surfactants include, without limitation, synthetic or natural phospholipids, PEGylated lipids (e.g., PEGylated phospholipid), lipid derivatives, polysorbates, amphiphilic copolymers, amphiphilic block copolymers, poly(ethylene glycol)-co-poly(lactide-co-glycolide) (PEG-PLGA), their derivatives, ligand-conjugated derivatives and combinations thereof. Other polymers or surfactants and their combinations that can form stable nanosuspensions and/or can chemically/physically bind to the targeting ligands of HIV infectable/infected CD4+ T cells, macrophages and dendritic cells can be used in the instant invention. Further examples of polymers or surfactants include, without limitation: 1) nonionic surfactants (e.g., pegylated and/or polysaccharide-conjugated polyesters and other hydrophobic polymeric blocks such as poly (lactide-co-glycolide) (PLGA), polylactic acid (PLA), polycaprolactone (PCL), other polyesters, poly(propylene oxide), poly(1,2-butylene oxide), poly(n-butylene oxide), poly(tetrahydrofurane), and poly(styrene); glyceryl esters, polyoxyethylene fatty alcohol ethers, polyoxyethylene sorbitan fatty acid esters, polyoxyethylene fatty acid esters, sorbitan esters, glycerol monostearate, polyethylene glycols, polypropyleneglycols, cetyl alcohol, cetostearyl alcohol, stearyl alcohol, aryl alkyl polyether alcohols, polyoxyethylene-polyoxypropylene copolymers, poloxamines, cellulose, methylcellulose, hydroxylmethylcellulose, hydroxypropylcellulose, hydroxypropylmethylcellulose, polysaccharides, starch and their derivatives, hydroxyethylstarch, polyvinyl alcohol (PVA), polyvinylpyrrolidone, and their combination thereof); and 2) ionic surfactants (e.g., phospholipids, amphiphilic lipids, 1,2-dialkylglycero-3-alkylphophocholines, 1, 2-distearoyl-sn-glecro-3-phosphocholine (DSPC), 1,2-distearoyl-sn-glycero-3-phosphoethanolamine-N-[carboxy(polyethylene glycol) (DSPE-PEG), dimethylaminoethanecarbamoyl cheolesterol (DC-Chol), N-[1-(2,3-Dioleoyloxy)propyl]-N,N,N-trimethylammonium (DOTAP), alkyl pyridinium halides, quaternary ammonium compounds, lauryldimethylbenzylammonium, acyl carnitine hydrochlorides, dimethyldioctadecylammonium (DDAB), n-octylamines, oleylamines, benzalkonium, cetyltrimethylammonium, chitosan, chitosan salts, poly(ethylenimine) (PEI), poly(N-isopropyl acrylamide) (PNIPAM), and poly (allylamine) (PAH), poly (dimethyldiallylammonium chloride) (PDDA), alkyl sulfonates, alkyl phosphates, alkyl phosphonates, potassium laurate, triethanolamine stearate, sodium lauryl sulfate, sodium dodecylsulfate, alkyl polyoxyethylene sulfates, alginic acid, alginic acid salts, hyaluronic acid, hyaluronic acid salts, gelatins, dioctyl sodium sulfosuccinate, sodium carboxymethylcellulose, cellulose sulfate, dextran sulfate and carboxymethylcellulose, chondroitin sulfate, heparin, synthetic poly(acrylic acid) (PAA), poly (methacrylic acid) (PMA), poly(vinyl sulfate) (PVS), poly(styrene sulfonate) (PSS), bile acids and their salts, cholic acid, deoxycholic acid, glycocholic acid, taurocholic acid, glycodeoxycholic acid, derivatives thereof, and combinations thereof.

The polymer or surfactant of the instant invention may be charged or neutral. In a particular embodiment, the polymer or surfactant is neutral or negatively charged (e.g., poloxamers, polysorbates, phospholipids, and their derivatives).

In a particular embodiment, the polymer or surfactant is an amphiphilic block copolymer or lipid derivative. In a particular embodiment, at least one polymer or surfactant of the nanoparticle is an amphiphilic block copolymer, particularly a copolymer comprising at least one block of poly (oxyethylene) and at least one block of poly(oxypropylene). In a particular embodiment, the polymer or surfactant is a triblock amphiphilic block copolymer. In a particular embodiment, the polymer or surfactant is a triblock amphiphilic block copolymer comprising a central hydrophobic block of polypropylene glycol flanked by two hydrophilic blocks of polyethylene glycol. In a particular embodiment, the surfactant is poloxamer 407.

In a particular embodiment, the amphiphilic block copolymer is a copolymer comprising at least one block of poly(oxyethylene) and at least one block of poly(oxypropylene). In a particular embodiment, the amphiphilic block copolymer is a poloxamer. Examples of poloxamers include, without limitation, Pluronic® L31, L35, F38, L42, L43, L44, L61, L62, L63, L64, P65, F68, L72, P75, F77, L81, P84, P85, F87, F88, L92, F98, L101, P103, P104, P105, F108, L121, L122, L123, F127, 10R5, 10R8, 12R3, 17R1, 17R2, 17R4, 17R8, 22R4, 25R1, 25R2, 25R4, 25R5, 25R8, 31R1, 31R2, and 31R4. In a particular embodiment, the poloxamer is poloxamer 407 (Pluronic® F127).

In a particular embodiment of the invention, the polymer or surfactant is present in the nanoparticle and/or solution to synthesize the nanoparticle (as described herein) at a concentration ranging from about 0.0001% to about 10% or 15% by weight. In a particular embodiment, the concentration of the polymer or surfactant ranges from about 0.01% to about 15%, about 0.01% to about 10%, about 0.1% to about 10%, or about 0.1% to about 6% by weight. In a particular embodiment, the nanoparticle comprises at least about 50%, 75%, 80%, 85%, 90%, 95%, 97%, 98%, 99% or higher therapeutic agent (prodrug) by weight. In a particular embodiment, the nanoparticles comprise a defined drug:polymer/surfactant ratio. In a particular embodiment, the drug:polymer/surfactant ratio (e.g., by weight) is from about 1:1 to about 1000:1, about 1:1 to about 10:1, about 10:6 to about 1000:6, about 20:6 to about 500:6, about 50:6 to about 200:6, or about 100:6.

As stated hereinabove, the polymer or surfactant of the instant invention may be linked to a targeting ligand. The targeting of the nanoparticles (e.g., to macrophage) can provide for superior targeting, decreased excretion rates, decreased toxicity, and prolonged half-life compared to free drug or non-targeted nanoparticles. A targeting ligand is a compound that specifically binds to a specific type of tissue or cell type (e.g., in a desired target:cell ratio). For example, a targeting ligand may be used for engagement or binding of a target cell (e.g., a macrophage, T cell, dendritic cell, etc.) surface marker or receptor which may facilitate its uptake into the cell (e.g., within a protected subcellular organelle that is free from metabolic degradation). In a particular embodiment, the targeting ligand is a ligand for a cell surface marker/receptor. The targeting ligand may be an antibody or antigen-binding fragment thereof immunologically specific for a cell surface marker (e.g., protein or carbohydrate) preferentially or exclusively expressed on the targeted tissue or cell type. The targeting ligand may be linked directly to the polymer or surfactant or via a linker. Generally, the linker is a chemical moiety comprising a covalent bond or a chain of atoms that covalently attaches the ligand to the polymer or surfactant. The linker can be linked to any synthetically feasible position of the ligand and the polymer or surfactant. Exemplary linkers may comprise at least one optionally substituted; saturated or unsaturated; linear, branched or cyclic aliphatic group, an alkyl group, or an optionally substituted aryl group. The linker may be a lower alkyl or aliphatic. The linker may also be a polypeptide (e.g., from about 1 to about 10 amino acids, particularly about 1 to about 5). In a particular embodiment, the targeting moiety is linked to either or both ends of the polymer or surfactant. The linker may be non-degradable and may be a covalent bond or any other chemical structure which cannot be substantially cleaved or cleaved at all under physiological environments or conditions.

The nanoparticles/nanoformulations of the instant invention may comprise targeted and/or non-targeted polymers or surfactants. In a particular embodiment, the molar ratio of targeted and non-targeted polymers or surfactants in the nanoparticles/nanoformulations of the instant invention is from about 0.001 to 100%, about 1% to about 99%, about 5% to about 95%, about 10% to about 90%, about 25% to about 75%, about 30% to about 60%, or about 40%. In a particular embodiment, the nanoparticle comprises only targeted polymers or surfactants. In a particular embodiment, the nanoparticles/nanoformulations of the instant invention comprise a folate targeted polymer or surfactant and a non-targeted version of the polymer or surfactant. In a particular embodiment, the nanoparticles/nanoformulations of the instant invention comprise folate-poloxamer 407 (FA-P407) and/or poloxamer 407.

Examples of targeting ligands include but are not limited to macrophage targeting ligands, CD4+ T cell targeting ligands, dendritic cell targeting ligands, and tumor targeting ligands. In a particular embodiment, the targeting ligand is a macrophage targeting ligand. The targeted nanoformulations of the instant invention may comprise a targeting ligand for directing the nanoparticles to HIV tissue and cellular sanctuaries/reservoirs (e.g., central nervous system, gut associated lymphoid tissues (GALT), CD4+ T cells, macrophages, dendritic cells, etc.). Macrophage targeting ligands include, without limitation, folate receptor ligands (e.g., folate (folic acid) and folate receptor antibodies and fragments thereof (see, e.g., Sudimack et al. (2000) Adv. Drug Del. Rev., 41:147-162)), mannose receptor ligands (e.g., mannose), formyl peptide receptor (FPR) ligands (e.g., N-formyl-Met-Leu-Phe (fMLF)), and tuftsin (the tetrapeptide Thr-Lys-Pro-Arg). Other targeting ligands include, without limitation, hyaluronic acid, gp120 and peptide fragments thereof, and ligands or antibodies specific for CD4, CCR5, CXCR4, CD7, CD111, CD204, CD49a, CD29, CD19, CD20, CD22, CD171, CD33, Leis-Y, WT-1, ROR1, MUC16, MUC1, MUC4, estrogen receptor, transferrin receptors, EGF receptors (e.g. HER2), folate receptor, VEGF receptor, FGF receptor, androgen receptor, NGR, Integrins, and GD2. In a particular embodiment, the targeting ligand is folic acid.

As stated hereinabove, the nanoparticles of the instant invention may comprise a further therapeutic agent. The instant invention also encompasses therapeutic methods wherein the prodrug and/or nanoparticles of the instant invention are co-administered with another therapeutic agent. In a particular embodiment, the therapeutic agent is hydrophobic, a water insoluble compound, or a poorly water soluble compound, particularly when included in the nanoparticle. For example, the therapeutic agent may have a solubility of less than about 10 mg/ml, less than 1 mg/ml, more particularly less than about 100 µg/ml, and more particularly less than about 25 µg/ml in water or aqueous media in a pH range of 0-14, preferably between pH 4 and 10, particularly at 20° C.

In a particular embodiment, the therapeutic agent is an antiviral or an antiretroviral. The antiretroviral may be effective against or specific to lentiviruses. Lentiviruses include, without limitation, human immunodeficiency virus (HIV) (e.g., HIV-1, HIV-2), bovine immunodeficiency virus (BIV), feline immunodeficiency virus (FIV), simian immunodeficiency virus (SIV), and equine infectious anemia virus (EIA). In a particular embodiment, the therapeutic agent is an anti-HIV agent. An anti-HIV compound or an anti-HIV agent is a compound which inhibits HIV (e.g., inhibits HIV replication and/or infection). Examples of anti-HIV agents include, without limitation:

(I) Nucleoside-analog reverse transcriptase inhibitors (NRTIs). NRTIs refer to nucleosides and nucleotides and analogues thereof that inhibit the activity of reverse transcriptase, particularly HIV-1 reverse transcriptase. NRTIs comprise a sugar and base. Examples of nucleoside-analog reverse transcriptase inhibitors include, without limitation, adefovir dipivoxil, adefovir, lamivudine, telbivudine, entecavir, tenofovir, stavudine, abacavir, didanosine, emtricitabine, zalcitabine, and zidovudine.

(II) Non-nucleoside reverse transcriptase inhibitors (NNRTIs). NNRTIs are allosteric inhibitors which bind reversibly at a nonsubstrate-binding site on reverse transcriptase, particularly the HIV reverse transcriptase, thereby altering the shape of the active site or blocking polymerase activity. Examples of NNRTIs include, without limitation, delavirdine (DLV, BHAP, U-90152; Rescriptor®), efavirenz (EFV, DMP-266, SUSTIVA®), nevirapine (NVP, Viramune®), PNU-142721, capravirine (S-1153, AG-1549), emivirine (+)-calanolide A (NSC-675451) and B, etravirine (ETR, TMC-125, Intelence®), rilpivirne (RPV, TMC278, Edurant™) DAPY (TMC120), doravirine (Pifeltro™), BILR-355 BS, PHI-236, and PHI-443 (TMC-278).

(III) Protease inhibitors (PI). Protease inhibitors are inhibitors of a viral protease, particularly the HIV-1 protease. Examples of protease inhibitors include, without limitation, darunavir, amprenavir (141W94, AGENERASE®), tipranivir (PNU-140690, APTIVUS®), indinavir (MK-639; CRIXIVAN®), saquinavir (INVIRASE®, FORTOVASEO), fosamprenavir (LEXIVA®), lopinavir (ABT-378), ritonavir (ABT-538, NORVIR®), atazanavir (REYATAZ®), nelfinavir (AG-1343, VIRACEPT®), lasinavir (BMS-234475/CGP-61755), BMS-2322623, GW-640385X (VX-385), AG-001859, and SM-309515.

(IV) Fusion or entry inhibitors. Fusion or entry inhibitors are compounds, such as peptides, which block HIV entry into a cell (e.g., by binding to HIV envelope protein and blocking the structural changes necessary for the virus to fuse with the host cell). Examples of fusion inhibitors include, without limitation, CCR5 receptor antagonists (e.g., maraviroc (Selzentry®, Celsentri)), enfuvirtide (INN, FUZEON®), T-20 (DP-178, FUZEON®) and T-1249.

(V) Integrase inhibitors (in addition to the prodrug of the instant invention). Integrase inhibitors are a class of antiretroviral drug designed to block the action of integrase (e.g., HIV integrase), a viral enzyme that inserts the viral genome into the DNA of the host cell. Examples of integrase inhibitors include, without limitation, raltegravir, elvitegravir, GSK1265744 (cabotegravir), GSK1349572 (dolutegravir), GS-9883 (bictegravir), and MK-2048.

Anti-HIV compounds also include maturation inhibitors (e.g., bevirimat). Maturation inhibitors are typically compounds which bind HIV gag and disrupt its processing during the maturation of the virus. Anti-HIV compounds also include HIV vaccines such as, without limitation, ALVAC® HIV (vCP1521), AIDSVAX® B/E (gp120), and combinations thereof. Anti-HIV compounds also include HIV antibodies (e.g., antibodies against gp120 or gp41), particularly broadly neutralizing antibodies.

More than one anti-HIV agent may be used, particularly where the agents have different mechanisms of action (as outlined above). For example, anti-HIV agents which are not NNRTIs may be combined with the NNRTI prodrugs of the instant invention. In a particular embodiment, the anti-HIV therapy is highly active antiretroviral therapy (HAART).

The instant invention encompasses compositions (e.g., pharmaceutical compositions) comprising at least one prodrug and/or nanoparticle of the instant invention and at least one pharmaceutically acceptable carrier. As stated hereinabove, the nanoparticle may comprise more than one therapeutic agent. In a particular embodiment, the pharmaceutical composition comprises a first nanoparticle comprising a first prodrug and a second nanoparticle comprising a second prodrug, wherein the first and second prodrugs are different. In a particular embodiment, the first prodrug is a prodrug of the instant invention and the second prodrug is a prodrug of a non-nucleoside reverse transcriptase inhibitor (NNRTI), particularly rilpivirine (RPV). The compositions (e.g., pharmaceutical compositions) of the instant invention may further comprise other therapeutic agents (e.g., other anti-HIV compounds (e.g., those described herein)).

The present invention also encompasses methods for preventing, inhibiting, and/or treating a disease or disorder. The methods comprise administering a prodrug and/or nanoparticle of the instant invention (optionally in a composition) to a subject in need thereof. In a particular embodiment, the disease or disorder is a viral (e.g., retroviral) infection. Examples of viral infections include, without limitation: HIV, Hepatitis B, Hepatitis C, and HTLV. In a particular embodiment, the viral infection is a retroviral or lentiviral infection, particularly an HIV infection (e.g., HIV-1).

The prodrugs and/or nanoparticles of the instant invention (optionally in a composition) can be administered to an animal, in particular a mammal, more particularly a human, in order to treat/inhibit/prevent the disease or disorder (e.g., a retroviral infection such as an HIV infection). The pharmaceutical compositions of the instant invention may also comprise at least one other therapeutic agent such as an antiviral agent, particularly at least one other anti-HIV compound/agent. The additional anti-HIV compound may also be administered in a separate pharmaceutical composition from the prodrugs or compositions of the instant invention. The pharmaceutical compositions may be administered at the same time or at different times (e.g., sequentially).

The dosage ranges for the administration of the prodrugs, nanoparticles, and/or compositions of the invention are those large enough to produce the desired effect (e.g., curing, relieving, treating, and/or preventing the disease or disorder (e.g., HIV infection), the symptoms of it (e.g., AIDS, ARC), or the predisposition towards it). In a particular embodiment, the pharmaceutical composition of the instant invention is administered to the subject at an amount from about 5 µg/kg to about 500 mg/kg. In a particular embodiment, the pharmaceutical composition of the instant invention is administered to the subject at an amount greater than about 5 µg/kg, greater than about 50 µg/kg, greater than about 0.1 mg/kg, greater than about 0.5 mg/kg, greater than about 1 mg/kg, or greater than about 5 mg/kg. In a particular embodiment, the pharmaceutical composition of the instant invention is administered to the subject at an amount from about 0.5 mg/kg to about 100 mg/kg, about 10 mg/kg to about 100 mg/kg, or about 15 mg/kg to about 50 mg/kg. The dosage should not be so large as to cause significant adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications.

The prodrugs and nanoparticles described herein will generally be administered to a patient as a pharmaceutical composition. The term "patient" as used herein refers to human or animal subjects. These prodrugs and nanoparticles may be employed therapeutically, under the guidance of a physician.

The pharmaceutical compositions comprising the prodrugs and/or nanoparticles of the instant invention may be conveniently formulated for administration with any pharmaceutically acceptable carrier(s). For example, the complexes may be formulated with an acceptable medium such as water, buffered saline, ethanol, polyol (for example, glycerol, propylene glycol, liquid polyethylene glycol and the like), dimethyl sulfoxide (DMSO), oils, detergents, suspending agents, or suitable mixtures thereof, particularly an aqueous solution. The concentration of the prodrugs and/or nanoparticles in the chosen medium may be varied and the medium may be chosen based on the desired route of administration of the pharmaceutical composition. Except insofar as any conventional media or agent is incompatible with the nanoparticles to be administered, its use in the pharmaceutical composition is contemplated.

The dose and dosage regimen of prodrugs and/or nanoparticles according to the invention that are suitable for administration to a particular patient may be determined by a physician considering the patient's age, sex, weight, general medical condition, and the specific condition for which the nanoparticles are being administered and the severity thereof. The physician may also take into account the route of administration, the pharmaceutical carrier, and the nanoparticle's biological activity.

Selection of a suitable pharmaceutical composition will also depend upon the mode of administration chosen. For example, the nanoparticles of the invention may be administered by direct injection or intravenously. In this instance, a pharmaceutical composition comprises the prodrug and/or nanoparticle dispersed in a medium that is compatible with the site of injection.

Prodrugs and/or nanoparticles of the instant invention may be administered by any method. For example, the prodrugs and/or nanoparticles of the instant invention can be administered, without limitation parenterally, subcutaneously, orally, topically, pulmonarily, rectally, vaginally, intravenously, intraperitoneally, intrathecally, intracerebrally, epidurally, intramuscularly, intradermally, or intracarotidly. In a particular embodiment, the prodrug and/or nanoparticle is parenterally. In a particular embodiment, the prodrug and/or nanoparticle is administered orally, intramuscularly, subcutaneously, or to the bloodstream (e.g., intravenously). In a particular embodiment, the prodrug and/or nanoparticle is administered intramuscularly or subcutaneously. Pharmaceutical compositions for injection are known in the art. If injection is selected as a method for administering the prodrug and/or nanoparticle, steps must be taken to ensure that sufficient amounts of the molecules or cells reach their target cells to exert a biological effect. Dosage forms for oral administration include, without limitation, tablets (e.g., coated and uncoated, chewable), gelatin capsules (e.g., soft or hard), lozenges, troches, solutions, emulsions, suspensions, syrups, elixirs, powders/granules (e.g., reconstitutable or dispersible) gums, and effervescent tablets. Dosage forms for parenteral administration include, without limitation, solutions, emulsions, suspensions, dispersions and powders/granules for reconstitution. Dosage forms for topical administration include, without limitation, creams, gels, ointments, salves, patches and transdermal delivery systems.

Pharmaceutical compositions containing a prodrug and/or nanoparticle of the present invention as the active ingredient in intimate admixture with a pharmaceutically acceptable carrier can be prepared according to conventional pharmaceutical compounding techniques. The carrier may take a wide variety of forms depending on the form of pharmaceutical composition desired for administration, e.g., intravenous, oral, direct injection, intracranial, and intravitreal.

A pharmaceutical composition of the invention may be formulated in dosage unit form for ease of administration and uniformity of dosage. Dosage unit form, as used herein, refers to a physically discrete unit of the pharmaceutical composition appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. In a particular embodiment, the prodrugs and/or nanoparticles of the instant invention, due to their long-acting therapeutic effect, may be administered once every 1 to 12 months or even less frequently. For example, the nanoformulations of the instant invention may be administered once every 0.5, 1, 2, 3, 4, 5, 6, 7, 8, 9, 10, 11, 12, 15, 18, 21, 24, or more months. In a particular embodiment, the prodrugs and/or nanoparticles of the instant invention are administered less than once every two months. In a particular embodiment, the prodrugs and/or nanoformulations of the prodrugs are administered once every month, once every two months, particularly once every three months, once every four months, once every five months, once every six months, once every seven months, once every eight months, once every nine months, once every ten months, once every eleven months, once every twelve months, or less frequently.

Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of nanoparticles may be determined by evaluating the toxicity of the molecules or cells in animal models. Various concentrations of nanoparticles in pharmaceutical composition may be administered to mice, and the minimal and maximal dosages may be determined based on the beneficial results and side effects observed as a result of the treatment. Appropriate dosage unit may also be determined by assessing the efficacy of the nanoparticle treatment in combination with other standard drugs. The dosage units of nanoparticle may be determined individually or in combination with each treatment according to the effect detected.

The pharmaceutical composition comprising the nanoparticles may be administered at appropriate intervals until the pathological symptoms are reduced or alleviated, after which the dosage may be reduced to a maintenance level. The appropriate interval in a particular case would normally depend on the condition of the patient.

The instant invention encompasses methods of treating a disease/disorder comprising administering to a subject in need thereof a pharmaceutical composition comprising a prodrug and/or nanoparticle of the instant invention and, preferably, at least one pharmaceutically acceptable carrier. The instant invention also encompasses methods wherein the subject is treated via ex vivo therapy. In particular, the method comprises removing cells from the subject, exposing/contacting the cells in vitro to the nanoparticles of the instant invention, and returning the cells to the subject. In a particular embodiment, the cells comprise macrophage. Other methods of treating the disease or disorder may be combined with the methods of the instant invention may be co-administered with the pharmaceutical compositions of the instant invention.

The instant also encompasses delivering the nanoparticle of the instant invention to a cell in vitro (e.g., in culture). The nanoparticle may be delivered to the cell in at least one carrier.

Definitions

The following definitions are provided to facilitate an understanding of the present invention.

The singular forms "a," "an," and "the" include plural referents unless the context clearly dictates otherwise.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin (Mack Publishing Co., Easton, PA); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

The term "prodrug" refers to a compound that is metabolized or otherwise converted to a biologically active or more active compound or drug, typically after administration. A prodrug, relative to the drug, is modified chemically in a manner that renders it, relative to the drug, less active, essentially inactive, or inactive. However, the chemical modification is such that the corresponding drug is generated by metabolic or other biological processes, typically after the prodrug is administered.

The term "treat" as used herein refers to any type of treatment that imparts a benefit to a patient afflicted with a disease, including improvement in the condition of the patient (e.g., in one or more symptoms), delay in the progression of the condition, etc. In a particular embodiment, the treatment of a retroviral infection results in at least an inhibition/reduction in the number of infected cells and/or detectable viral levels.

As used herein, the term "prevent" refers to the prophylactic treatment of a subject who is at risk of developing a condition (e.g., HIV infection) resulting in a decrease in the probability that the subject will develop the condition.

A "therapeutically effective amount" of a compound or a pharmaceutical composition refers to an amount effective to prevent, inhibit, treat, or lessen the symptoms of a particular disorder or disease. The treatment of a microbial infection (e.g., HIV infection) herein may refer to curing, relieving, and/or preventing the microbial infection, the symptom(s) of it, or the predisposition towards it.

As used herein, the term "therapeutic agent" refers to a chemical compound or biological molecule including, without limitation, nucleic acids, peptides, proteins, and antibodies that can be used to treat a condition, disease, or disorder or reduce the symptoms of the condition, disease, or disorder.

As used herein, the term "small molecule" refers to a substance or compound that has a relatively low molecular weight (e.g., less than 4,000, less than 2,000, particularly less than 1 kDa or 800 Da). Typically, small molecules are organic, but are not proteins, polypeptides, or nucleic acids, though they may be amino acids or dipeptides.

The term "antimicrobials" as used herein indicates a substance that kills or inhibits the growth of microorganisms such as bacteria, fungi, viruses, or protozoans.

As used herein, the term "antiviral" refers to a substance that destroys a virus and/or suppresses replication (reproduction) of the virus. For example, an antiviral may inhibit and or prevent: production of viral particles, maturation of viral particles, viral attachment, viral uptake into cells, viral assembly, viral release/budding, viral integration, etc.

As used herein, the term "highly active antiretroviral therapy" (HAART) refers to HIV therapy with various combinations of therapeutics such as nucleoside reverse transcriptase inhibitors, non-nucleoside reverse transcriptase inhibitors, HIV protease inhibitors, and fusion inhibitors.

As used herein, the term "amphiphilic" means the ability to dissolve in both water and lipids/apolar environments. Typically, an amphiphilic compound comprises a hydrophilic portion and a hydrophobic portion. "Hydrophobic" designates a preference for apolar environments (e.g., a hydrophobic substance or moiety is more readily dissolved in or wetted by non-polar solvents, such as hydrocarbons, than by water). "Hydrophobic" compounds are, for the most part, insoluble in water. As used herein, the term "hydrophilic" means the ability to dissolve in water.

As used herein, the term "polymer" denotes molecules formed from the chemical union of two or more repeating units or monomers. The term "block copolymer" most simply refers to conjugates of at least two different polymer segments, wherein each polymer segment comprises two or more adjacent units of the same kind.

An "antibody" or "antibody molecule" is any immunoglobulin, including antibodies and fragments thereof (e.g., scFv), that binds to a specific antigen. As used herein, antibody or antibody molecule contemplates intact immunoglobulin molecules, immunologically active portions of an immunoglobulin molecule, and fusions of immunologically active portions of an immunoglobulin molecule.

As used herein, the term "immunologically specific" refers to proteins/polypeptides, particularly antibodies, that bind to one or more epitopes of a protein or compound of interest, but which do not substantially recognize and bind other molecules in a sample containing a mixed population of antigenic biological molecules.

As used herein, the term "targeting ligand" refers to any compound which specifically binds to a specific type of tissue or cell type, particularly without substantially binding other types of tissues or cell types. Examples of targeting ligands include, without limitation: proteins, polypeptides, peptides, antibodies, antibody fragments, hormones, ligands, carbohydrates, steroids, nucleic acid molecules, and polynucleotides.

The term "aliphatic" refers to a non-aromatic hydrocarbon-based moiety. Aliphatic compounds can be acyclic (e.g., linear or branched) or cyclic moieties (e.g., cycloalkyl) and can be saturated or unsaturated (e.g., alkyl, alkenyl, and alkynyl). Aliphatic compounds may comprise a mostly carbon main chain (e.g., 1 to about 30 carbons) and comprise heteroatoms and/or substituents (see below). The term "alkyl," as employed herein, includes saturated or unsaturated, straight or branched chain hydrocarbons containing 1 to about 30 carbons in the normal/main chain. The hydrocarbon chain of the alkyl groups may be interrupted with one or more heteroatom (e.g., oxygen, nitrogen, or sulfur). An alkyl (or aliphatic) may, optionally, be substituted (e.g. with fewer than about 8, fewer than about 6, or 1 to about 4 substituents). The term "lower alkyl" or "lower aliphatic" refers to an alkyl or aliphatic, respectively, which contains 1 to 3 carbons in the hydrocarbon chain. Alkyl or aliphatic substituents include, without limitation, alkyl (e.g., lower alkyl), alkenyl, halo (such as F, Cl, Br, I), haloalkyl (e.g., $CCl_3$ or $CF_3$), alkoxyl, alkylthio, hydroxy, methoxy, carboxyl, oxo, epoxy, alkyloxycarbonyl, alkylcarbonyloxy, amino, carbamoyl (e.g., $NH_2C(=O)$— or $NHRC(=O)$—, wherein R is an alkyl), urea (—$NHCONH_2$), alkylurea, aryl, ether, ester, thioester, nitrile, nitro, amide, carbonyl, carboxylate and thiol. Aliphatic and alkyl groups having at least about 5 carbons in the main chain are generally hydrophobic, absent extensive substitutions with hydrophilic substituents.

The term "aryl," as employed herein, refers to monocyclic and bicyclic aromatic groups containing 6 to 10 carbons in the ring portion. Examples of aryl groups include, without limitation, phenyl or naphthyl, such as 1-naphthyl and 2-naphthyl, or indenyl. Aryl groups may optionally include one to three additional rings fused to a cycloalkyl ring or a heterocyclic ring. Aryl groups may be optionally substituted through available carbon atoms with, for example, 1, 2, or 3 groups selected from hydrogen, halo, alkyl, polyhaloalkyl, alkoxy, alkenyl, trifluoromethyl, trifluoromethoxy, alkynyl, aryl, heterocyclo, aralkyl, aryloxy, aryloxyalkyl, aralkoxy, arylthio, arylazo, heterocyclooxy, hydroxy, nitro, cyano, sulfonyl anion, amino, or substituted amino. The aryl group may be a heteroaryl. "Heteroaryl" refers to an optionally substituted, mono-, di-, tri-, or other multicyclic aromatic ring system that includes at least one, and preferably from 1 to about 4, sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred.

The following examples provide illustrative methods of practicing the instant invention and are not intended to limit the scope of the invention in any way.

Example 1

Maximal reduction of residual HIV-1 from its tissue sanctuary sites that include brain, lymph nodes, bone marrow, gut-associated lymphoid tissue and the genital tracts can be achieved by development of long acting reservoir targeted medicines. In addition to the benefit of infrequent dosing intervals, long acting injectable drug formulations can be designed to utilize receptor mediated processes to achieve improved cell targeting, extended drug half-life, and enhanced tissue biodistribution. CAB is a potent viral integrase inhibitor and has been formulated as a LAP (CAB-LAP) which demonstrates sustained plasma drug levels in humans after single intramuscular dose. Long-acting injectable nanoformulations of rilpivirine and CAB-LAP have already enabled once-monthly injection for HIV suppression and prevention (Andrews, et al. (2014) Science 343(6175): 1151-1154; Cohen, J. (2014) Science 343(6175):1067; Spreen, et al. (2013) Curr. Opin. HIV AIDS, 8(6):565-571). The main limitations of existing nanoformulations include requirement for high doses and high injection volumes. To this end, long acting slow effective release antiretroviral therapies (LASER ART) have been developed by synthesizing lipophilic and hydrophobic prodrug nanocrystals that permit rapid drug penetration across physiological barriers (Lin, et al. (2018) Chem. Commun. (Camb) 54:8371-4; Montenegro-Burke, et al. (2018) J R, Woldstad C J, Fang M, Bade A N, McMillan J, Edagwa B, et al. (2018) Mol. Neurobiol., 56(4):2896-2907; Thomas, et al., (2018) M B, Gnanadhas D P, Dash P K, Machhi J, Lin Z, McMillan J, et al. (2018) Nanomedicine (Lond) 13(17):2139-2154; Gu, et al. (2018) PLoS Pathog., 14:e1007061; Zhou, et al. (2018) Biomaterials 151:53-65; Kevadiya, et al. (2018) Theranostics 8:256-76; Sillman, et al. (2018) Nat. Commun., 9:443; McMillan, et al. (2018) Antimicrob. Agents Chemother., 62: e01316-17; Gnanadhas, et al. (2017) J. Clin. Invest., 127: 857-73). LASER ART maximizes drug loading with limited excipient usage, while maintaining scalability and long-term storage. Myristoylated prodrugs have been formulated with poloxamer surfactants. Improved potency, bioavailability, and tissue distribution of CAB was demonstrated by increasing drug lipophilicity that sustained plasma CAB concentrations at the PA-$IC_{90}$ for 4 months in rhesus macaques after single 45 mg/kg CAB equivalent intramuscular injection. Here, improved prodrugs and nanoformulations have been synthesized which reduce dosing frequency while improving viral reservoir targeting and drug activity.

Fatty diester and monoester integrase inhibitor prodrugs are provided herein. Fatty ester CAB dimers and substitution with amino acid fatty esters can extend the injecting dosing intervals from >6 months to a year. These integrase inhibitor formulations will reduce injection volumes and readily cross-cell and tissue barriers. Optimal use of lipophilic drug nanocrystals will facilitate macrophage and CD4+ T cell particle uptake. Integrase inhibitors will be modified, for example, using azeloyl and steroyl diacids, alanyl and phenylalanyl palmitoyl esters. Lipophilic prodrugs will enhance intracellular delivery of the integrase inhibitor and improve potency. One means of decreasing injection volumes is through positively affecting drug potency. The proposed ester derivatizing promoieties are biocompatible and as such adjust to their microenvironment (Remenar, J. F. (2014) Mol. Pharm., 11:1739-49). The hydrocarbon chain length will tightly control prodrug bioconversion, while hydrophobic amino acid side chains improve drug to polymer interactions affecting formulation stability and intracellular prodrug hydrolysis (Remenar, J. F. (2014) Mol. Pharm., 11:1739-49; Ikuta, et al. (2015) Chem. Commun. (Camb) 51:12835-8). Abilities to control drug release by changing dimer design allows drug release rates and activation to be tuned depending on the prodrug and particle. Slow prodrug conversion in blood also allows the drug to redistribute into tissue rather than causing spikes and troughs in active CAB concentration. Amino acid modified esters not only improve prodrug and formulation stability but have also facilitate active transport of active compounds across cell membranes (Vig, et al. (2003) Pharm. Res., 20:1381-8). Cell and tissue targeted formulations will optimize drug entry and retention. Dissolution rates of drug and subsequent diffusion into extracellular media will control rate of release and prodrug bioconversion.

Fatty diester CAB (M3CAB and M4CAB) and amino acid modified fatty ester CAB prodrugs (MSCAB and M6CAB) will be synthesized using a one-step scalable synthesis scheme (Zhou, et al. (2018) Biomaterials 151:53-65; Sillman, et al. (2018) Nat. Commun., 9:443). Briefly, the parent drug will be dissolved in dimethylformamide, followed by deprotonation with N,N-diisopropyethylamine base and conjugation to fatty acyl chlorides under an inert atmosphere (FIG. 1).

Prodrug chemical structures and crystallinity will be evaluated by nuclear magnetic resonance (NMR), Fourier-transform infrared spectroscopy (FTIR), mass spectrometry (MS), and X-ray diffraction (XRD). Prodrug potency is linked to cleavage of derivatizing promoieties (Birkus, et al. (2008) Mol. Pharmacol., 74:92-100; Birkus, et al. (2007) Antimicrob. Agents Chemother., 51:543-50; Feng, et al. (2018) Antimicrob. Agents Chemother., 62: e00620-18; Okon, et al. (2017) ACS Med. Chem. Lett., 8:958-62; McGuigan, et al. (2010) J. Med. Chem., 53:4949-57). Enzymatic and chemical stability studies will be performed to determine prodrug hydrolysis, metabolic activation and efficacy. The compounds will be dissolved in sera of multiple species and buffers followed by prodrug and active drug quantitation by mass spectrometry. Prodrug metabolism in liver homogenates and hepatocytes from rat, rabbit, dog and human will be determined (Hoppe, et al. (2014) J. Pharm. Sci., 103:1504-14). Intracellular activation of the synthesized prodrugs in subcellular compartments in the presence and absence of various cathepsin and peptidase inhibitors will also be determined. The role of hydrolytic enzymes in ester bond cleavage will be assessed in efficacy studies that will include determination of $EC_{50}$ of each compound in MDM and CD4+ T cells. Prodrugs will then proceed to formulation-screening phase where compound solubility profile, thermal and chemical properties will be evaluated to establish excipient compatibility and potential drug release profiles. CAB apparent half-life will be extended by transformation into lipophilic CAB prodrugs. Prodrug formation is at the core of strategy reflecting masked forms of native drugs that become activated through enzymatic and/or chemical hydrolysis with no change in pharmacological outcomes (Huttunen, et al. (2011) Pharmacol. Rev., 63:750-71; Anastasi, et al. (2003) Curr. Med. Chem., 10:1825-43). Prodrugs offer therapeutic benefits over native compounds with reduced pre-systemic metabolism and toxicity and increased lipophilicity for enhanced cell membrane and tissue permeability (Rautio, et al. (2008) Nat. Rev. Drug Discov., 7:255-70; Park, et al. (2013) Arch. Pharm. Res., 36:651-9).

Particle uptake, retention, release and sustained antiretroviral activities in both MDM and CD4+ T cells will also be evaluated. First, MDM will be treated with the prodrug formulations. These will be tested for uptake (2 to 24 hours), retention, release, and antiretroviral activities (1 to 30 days). Drug content in MDM will be quantified by high performance liquid chromatography (HPLC). Antiretroviral drug activity tests will be performed by measures of RT activity and cell-associated HIV-1 p24 in cells previously challenged with virus (ADA or other CCR5 strains such as DJV and Yu2). Cells will first be given prodrug formulations then challenged with virus from one to 30 days. Native drug formulation treatments will serve as controls.

Antiretroviral, immune, and neuroprotective outcomes in humanized mice will be assessed at the tissue and cellular levels. Immune deficient mice transplanted with CD34+ hematopoietic stem cells will be used to assess whether nanoformulations could reach sanctuary sites to protect mice from infection (Gorantla, et al. (2012) J. Neuroimmune Pharmacol., 7(2):352-62; Gorantla, et al. (2010) Am. J. Pathol., 177:2938-49; Dash, et al. (2011) J. Neurosci., 31:3148-57; Gorantla, et al. (2010) J. Immunol., 184:7082-91; Gorantla, et al. (2007) J. Virol., 81:2700-12). Humanized mice will be administered a single IM dose of ARV formulations at a concentration of 45 mg/kg at 22 weeks of age. Mice will be challenged two weeks post drug treatment with $2 \times 10^4$ $TCID_{50}$ of HIV-$1_{ADA}$ by IP injection. Plasma will be used for quantitative viral load measurements. PrEP tests will be performed in mice challenged up to one year. Following study termination, spleen, thymus, lymph nodes, liver, lungs, gut, genitourinary tissues, and brain will be collected at 3, 6, 9 and 12 months for drug quantitation and cell profiling. HIV-1p24 staining, nested and droplet digital PCR, DNA and RNA scope, and viral load will be measured.

Example 2

The DTG prodrugs M3DTG and M4DTG were studied. First, antiretroviral efficacy was determined by measurement of HIV reverse transcriptase (RT) activity. To assess antiretroviral efficacy, monocyte-derived macrophage (MDM) were treated with either M3DTG or M4DTG for 8 hours over a range of concentrations (0.01-1000 nM). Drug was dosed in 0.1% (v/v) DMSO in media. After treatment, cells were washed with PBS to remove excess of free drug and nanoparticles and the cells were cultured with fresh media, with half-media exchanges every other day. The MDM were challenged with HIV-$1_{ADA}$ at a MOI of 0.01 infectious viral particles/cell for up to 30 days. Progeny virion production was measured by RT activity in culture medium (Kalter, et al. (1992) J. Clin. Microbiol., 30(4):993-995). As seen in FIG. 2A, both M3DTG and M4DTG possess significant antiretroviral activity.

Nanoformulations were generated as follows. Drug nanocrystals were coated with poloxamer 407 (P407). The nanocrystals may also be stabilized with 1,2-distearoyl-sn-glycero-3-phosphocholine (DSPC), 1,2-distearoyl-sn-glycero-3-phosphoethanolamine-N-[carboxy(polyethylene glycol)-2000 (DSPE-PEG), and/or polyvinyl alcohol (PVA), polysorbate and/or polyethylene glycol surfactants. Briefly, drug and P407 were mixed in endotoxin free water. The premixed suspensions were formulated by wet milling or high-pressure homogenization at 20,000 psi pressure until desirable size and polydispersity index (PDI) were achieved.

Nanoformulations were characterized for particle size, polydispersity index (PDI) and zeta potential by dynamic light scattering (Table 1). This was done using a Malvern Zetasizer, Nano Series Nano-ZS (Malvern Instruments Inc, Westborough, MA). Nanoparticle morphology was determined by scanning electron microscopy (SEM). UPLC MS/MS was used for drug quantitation.

TABLE 1

Formulation characterization.

| Formulation | Buffer | Drug: Polymer | Purification | Size (nm) | PDI | Zeta (mV) |
|---|---|---|---|---|---|---|
| NDTG | Water | 2:1 | Centrifugation | 358 | 0.25 | −8.6 |
| NM3DTG | 10 mM HEPES, pH 7.8 | 2:1 | Centrifugation | 277 | 0.22 | −34.3 |
| NM4DTG | 10 mM HEPES, pH 7.8 | 2:1 | Centrifugation | 370 | 0.32 | −31.8 |

Cell vitality was also assessed. Briefly, cellular viability following treatment with nanoparticles was evaluated by performing a 3-(4,5-dimethylthiazol-2-yl)-2,5-diphenyltetrazolium bromide (MTT) assay. Human MDM plated in 96-well plates at a density of $0.08 \times 10^6$ cells per well were treated with various concentrations of nanoparticles for 24 hours. Untreated cells were used as controls. For each group samples were in quadruplets. Cells were washed with PBS and incubated with 100 μL/well of MTT solution (5 mg/mL) for 45 minutes at 37° C. After incubation, MTT solution was removed, and cells were washed with PBS. Then, 200 μL of DMSO was added to each well, and absorbance was measured at 490 nm on a Molecular Devices SpectraMax® M3 plate reader with SoftMax Pro 6.2 software (Sunnyvale, CA). As seen in FIG. 2B, neither NM3DTG nor NM4DTG were toxic to the MDM cells.

Drug uptake and retention were also measured. Human monocytes were plated in a 12-well plate at a density of $1.0 \times 10^6$ cells per well using DMEM supplemented with 10% heat-inactivated pooled human serum, 1% glutamine, 10 μg/mL ciprofloxacin, and 50 μg/mL gentamicin. Cells were maintained at 37° C. in a 5% $CO_2$ incubator. After 7-10 days of differentiation in the presence of 1000 U/mL recombinant human macrophage colony stimulating factor (MCSF), MDM were treated with a range of nanoformulations. Uptake of drug was assessed by measurements of intracellular drug concentrations at various timepoints after treatment. For drug retention studies, cells were treated for 8 hours then washed with PBS and maintained with half-media changes every other day until collection at various timepoints. For both studies, adherent MDM were washed with PBS (3×1 mL), then scraped into 1 mL of fresh PBS, and counted at indicated time points using a Countess™ automated cell counter (Invitrogen, Carlsbad, CA). Cells were pelleted by centrifugation at 4° C. The cell pellet was reconstituted in high performance liquid chromatography (HPLC)-grade methanol and probe sonicated followed by centrifugation. The supernatant was analyzed for drug content using HPLC. DTG levels were measured for NDTG treatment, while prodrug levels were measured for prodrug formulation treatments.

As seen in FIG. 3, NM3DTG and NM4DTG were taken up by MDM to dramatically higher levels than NDTG. Moreover, MDM retained NM3DTG and NM4DTG at dramatically higher levels for longer periods of time than NDTG (FIG. 4).

Antiretroviral efficacy was also determined in MDM by HIV-1 RT activity up to 30 days after drug treatment (FIG. 5). Cells were pretreated for 8 hours with equal drug concentrations of 1 μM or 10 μM NM3DTG or NM4DTG. At the indicated times cells were challenged with HIV-1$_{ADA}$ and media was collected after an additional 10 days and assayed for HIV-1 RT activity. As seen in FIG. 5, NM3DTG and NM4DTG possess significant antiretroviral activity.

Pharmacokinetics (PK) studies in mice were also performed. BALB/cJ. (Male, 6-8 weeks, Jackson Labs) were administered 45 mg/kg DTG-equivalents of NDTG, NM3DTG, or NM4DTG by a single intramuscular (IM, caudal thigh muscle) injection. Following injection, blood samples were collected into heparinized tubes at day 1 post-administration and then weekly by cheek puncture (submandibular vein, MEDIpoint, Inc., Mineola, NY). Collected blood (25 μL) was immediately diluted into 1 mL ACN and stored at −80° C. until drug measurements. Remaining blood samples were centrifuged at 2,000 g for 8 minutes for plasma collection. Plasma was collected and stored at −80° C. for analysis of drug contents. DTG, M3DTG, and M4DTG were quantitated in mouse plasma by UPLC-MS/MS using a Waters ACQUITY H-class UPLC (Waters, Milford, MA, USA) connected to a Xevo TQ-S micro mass spectrometer. All solvents for sample processing and UPLC-MS/MS analysis were LCMS-grade (Fisher). 25 μL of sample was added into 1 mL acetonitrile (ACN) spiked with 10 μL internal standard (IS). Samples were vortexed and centrifuged at 17,000×g for 10 minutes at 4° C. The supernatants were collected and dried using a SpeedVac® and reconstituted in 100 μL 80% methanol; 10 μL was injected for DTG, M3DTG, and M4DTG UPLC-MS/MS analysis. Standard curves were prepared in blank mouse plasma/blood. Spectra were analyzed and quantified by MassLynx software version 4.1. All quantitations were determined using analyte peak area to internal standard peak area ratios.

As seen in FIG. 6A, all mice gained weight during the PK study, indicating good animal health. The plasma concentration of DTG or prodrug is shown in FIG. 6B. At day 1 post-injection, NDTG treatment generated higher plasma DTG concentrations compared to both NM3DTG and NM4DTG and showed dramatically faster decay kinetics over the study period in comparison to NM3DTG and NM4DTG. With NDTG treatment, plasma DTG concentrations were maintained above the four times protein-adjusted 90% inhibitory concentration (4×PA-$IC_{90}$) up to about day 20 (792.7 ng/mL), then rapidly declined to below the protein associated inhibitor concentration (PA-$IC_{90}$) by day 27 (75 ng/mL) before falling to near the limit of quantitation (0.5 ng/mL) by about day 56. NM3DTG treatment showed significantly slower decay, and maintained plasma DTG levels above the 4×PA-$IC_{90}$ up to about day 98 and above PA-$IC_{90}$ for the length of the experiment. NM4DTG treatment also showed significantly slower decay, and maintained plasma DTG levels above the 4×PA-$IC_{90}$ up to about day 112 and above PA-$IC_{90}$ for the length of the experiment. Thus, the data in FIG. 6B demonstrated that DTG half-life following NM3DTG or NM4DTG treatment was dramatically greater than that of NDTG.

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

The invention claimed is:

1. A compound, or a pharmaceutically acceptable salt or stereoisomer thereof, comprising:
   (a) a first bictegravir molecule;
   (b) a second bictegravir molecule; and
   (c) a linker, wherein the linker covalently attaches the first and second bictegravir molecules.

2. The compound of claim 1, or a pharmaceutically acceptable salt or stereoisomer thereof, wherein the linker is a diester comprising a saturated linear aliphatic chain of 16 carbons in length in between the ester of the diester, wherein the number of carbons does not include the carbon in the C=O of each ester of the diester, and wherein the hydroxy of each bictegravir is replaced by said ester of the diester.

3. A nanoparticle, comprising: (a) a compound of claim 1, or a pharmaceutically acceptable salt or stereoisomer thereof, and (b) a polymer or surfactant.

4. The nanoparticle of claim 3, wherein said polymer or surfactant is an amphiphilic block copolymer.

5. The nanoparticle of claim 4, wherein said amphiphilic block copolymer comprises at least one block of poly(oxyethylene) and at least one block of poly(oxypropylene).

6. The nanoparticle of claim 3, wherein said polymer or surfactant is P407.

7. The nanoparticle of claim 3, wherein said polymer or surfactant is polysorbate or polyethylene glycol.

8. A pharmaceutical composition, comprising: (a) a compound of claim 1, or a pharmaceutically acceptable salt or stereoisomer thereof, and (b) a pharmaceutically acceptable carrier.

* * * * *